(12) United States Patent
Grenier

(10) Patent No.: US 9,062,152 B2
(45) Date of Patent: Jun. 23, 2015

(54) ORGANIC ELECTRONIC DEVICES, INCLUDING ORGANIC PHOTOVOLTAIC DEVICES, POLYMERS, AND MONOMERS

(75) Inventor: Christophe René Gaston Grenier, Pittsburgh, PA (US)

(73) Assignee: SOLVAY USA, INC., Cranbury, NJ (US)

( * ) Notice: Subject to any disclaimer, the term of this patent is extended or adjusted under 35 U.S.C. 154(b) by 480 days.

(21) Appl. No.: 13/281,023

(22) Filed: Oct. 25, 2011

(65) Prior Publication Data
US 2012/0283377 A1 Nov. 8, 2012

Related U.S. Application Data

(63) Continuation-in-part of application No. 12/874,163, filed on Sep. 1, 2010, now Pat. No. 8,968,885.

(60) Provisional application No. 61/407,419, filed on Oct. 27, 2010.

(51) Int. Cl.

| | |
|---|---|
| C08G 75/06 | (2006.01) |
| C07D 333/50 | (2006.01) |
| C08K 5/03 | (2006.01) |
| C09D 11/00 | (2014.01) |
| C09D 145/00 | (2006.01) |
| C08G 61/12 | (2006.01) |
| C07D 487/04 | (2006.01) |
| C07D 495/04 | (2006.01) |
| C07D 495/06 | (2006.01) |
| C07D 495/22 | (2006.01) |
| C07D 519/00 | (2006.01) |
| C07F 7/08 | (2006.01) |
| C08L 65/00 | (2006.01) |
| C09D 11/52 | (2014.01) |
| C09D 165/00 | (2006.01) |
| H01L 51/00 | (2006.01) |
| C09B 57/00 | (2006.01) |
| C09B 69/00 | (2006.01) |
| C09B 69/10 | (2006.01) |
| H01L 51/42 | (2006.01) |

(52) U.S. Cl.
CPC ............ *C08G 61/126* (2013.01); *C07D 487/04* (2013.01); *C07D 495/04* (2013.01); *C07D 495/06* (2013.01); *C07D 495/22* (2013.01); *C07D 519/00* (2013.01); *C07F 7/0816* (2013.01); *C08G 61/12* (2013.01); *C08G 2261/124* (2013.01); *C08G 2261/18* (2013.01); *C08G 2261/226* (2013.01); *C08G 2261/228* (2013.01); *C08G 2261/3243* (2013.01); *C08G 2261/334* (2013.01); *C08G 2261/344* (2013.01); *C08G 2261/364* (2013.01); *C08G 2261/414* (2013.01); *C08G 2261/512* (2013.01); *C08G 2261/91* (2013.01); *C08L 65/00* (2013.01); *C09D 11/52* (2013.01); *C09D 165/00* (2013.01); *H01L 51/0036* (2013.01); *H01L 51/0043* (2013.01); *H01L 51/0069* (2013.01); *H01L 51/0077* (2013.01); *H01L 51/4253* (2013.01); *Y02E 10/549* (2013.01); *C09B 57/00* (2013.01); *C09B 69/008* (2013.01); *C09B 69/109* (2013.01)

(58) Field of Classification Search
None
See application file for complete search history.

(56) References Cited

U.S. PATENT DOCUMENTS

| | | | |
|---|---|---|---|
| 2009/0032808 A1 * | 2/2009 | Bazan et al. | 257/40 |
| 2009/0108255 A1 | 4/2009 | Bazan et al. | |
| 2009/0171048 A1 * | 7/2009 | Chan et al. | 526/256 |

FOREIGN PATENT DOCUMENTS

| | | |
|---|---|---|
| JP | 2009302470 A * | 12/2009 |
| WO | WO-2011/028827 A2 | 3/2011 |

OTHER PUBLICATIONS

Machine translation of JP2009-302470. Date of publication: Dec. 24, 2009.*
Written Opinion and Search Report mailed Jan. 31, 2012 in PCT/US2011/057662, 9 pages.

\* cited by examiner

*Primary Examiner* — Andrew K Bohaty
(74) *Attorney, Agent, or Firm* — The Marbury Law Group, PLLC

(57) ABSTRACT

Materials for organic electronic devices including organic photovoltaic devices. An oligomer or polymer comprising:

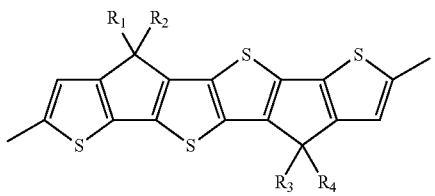

wherein $R_1$, $R_2$, $R_3$, and $R_4$ are independently hydrogen or solubilizing groups. Monomers and ink compositions can be also prepared. The materials can be used in an OPV active layer and show excellent absorption properties with bathochromic shift.

30 Claims, 4 Drawing Sheets

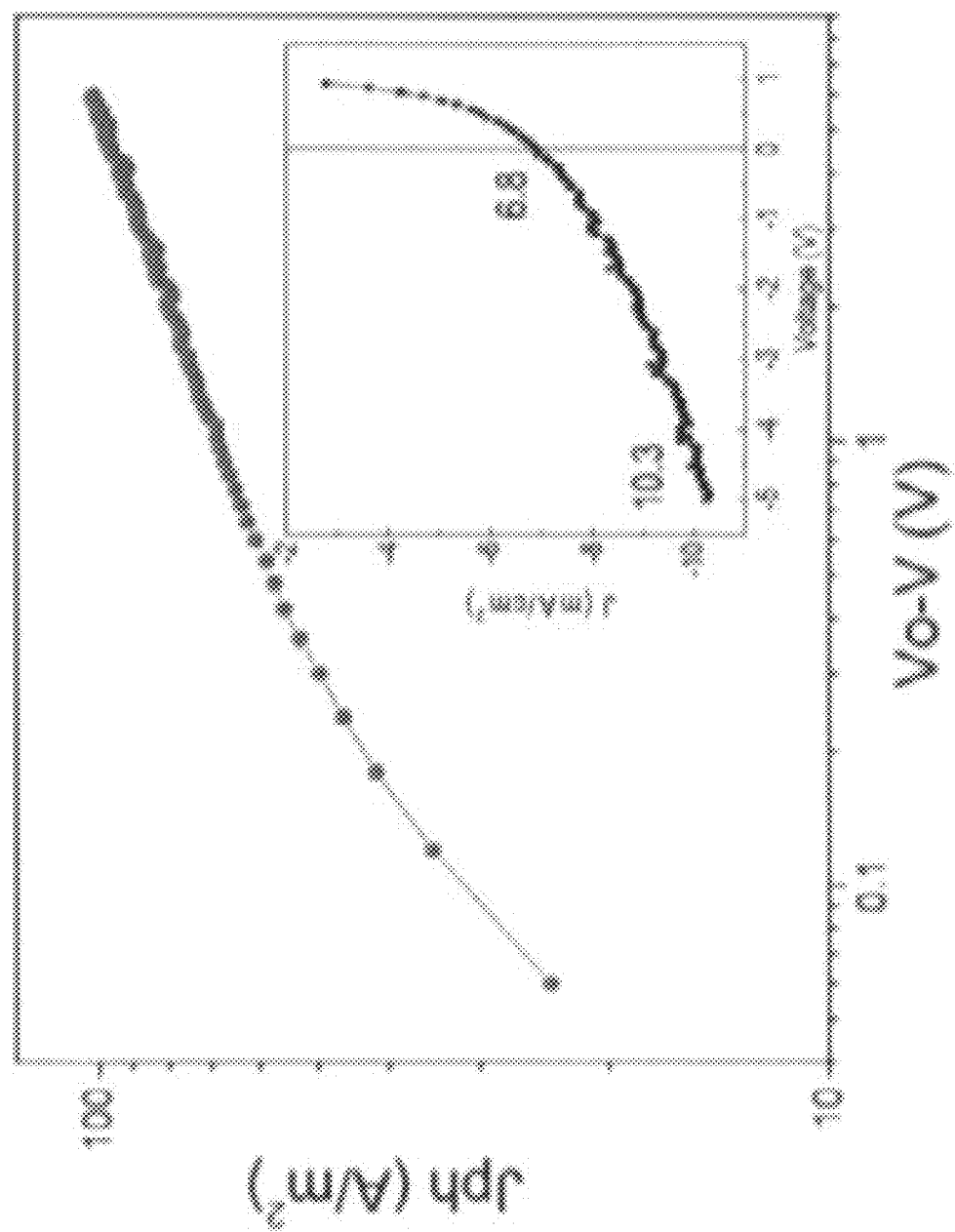
FIGURE 2 – CONTINUED

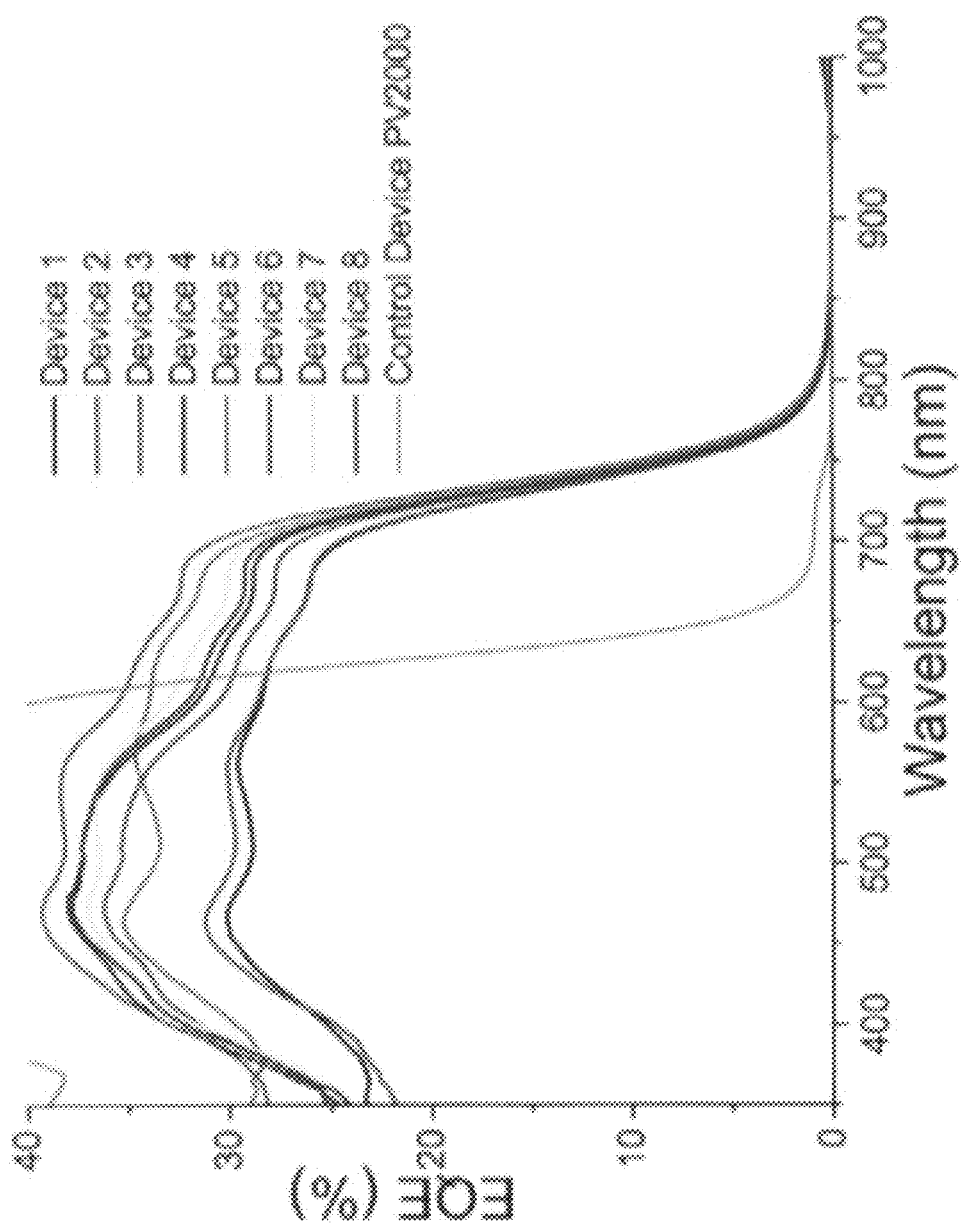

ORGANIC ELECTRONIC DEVICES, INCLUDING ORGANIC PHOTOVOLTAIC DEVICES, POLYMERS, AND MONOMERS

RELATED APPLICATIONS

This application is a continuation-in-part application claiming priority to U.S. regular application Ser. No. 12/874,163 filed Sep. 1, 2010 to Sheina et al., which is hereby incorporated by reference in its entirety. This application also claims priority to U.S. provisional application Ser. No. 61/407,419 filed Oct. 27, 2010, which is hereby incorporated by reference in its entirety.

INTRODUCTION

A need exists to provide better electronic and photonic devices including better solar cells or photovoltaic devices. If some aspects of the devices are based on organic materials, including organic polymers, cost reduction can be achieved.

In particular, a need exists to provide better active layers for organic photovoltaic devices. These active layers can comprise a combination of p-type material and n-type material. The p-type material can be a conjugated polymer. The polymer ideally should satisfy a variety of chemico-physical properties, such as solubility, processability, good film formation, proper absorption properties, proper HOMO/LUMO (molecular orbitals and energy levels), bandgap, charge carrier mobility, and other properties. However, achievement of combinations of properties can be difficult, and gaining one property may result in the sacrifice of another.

For a review of organic photovoltaic technology, see, for example, Sun and Saraciftci (Eds.), *Organic Photovoltaics, Mechanisms, Materials, and Devices*, CRC, 2005.

SUMMARY

Embodiments provided herein include, for example, compositions, devices, and methods of making and using the same. Compositions include, for example, monomer, oligomer, and polymer compositions, as well as ink formulations. Compositions also can include those prepared by particular processes. Devices include organic electronic devices including photovoltaic and/or solar cell devices including modules and devices which comprise a plurality of photovoltaic and/or solar cell devices. Coated substrates can be prepared, wherein the substrate is rigid or flexible.

For example, one embodiment provides an oligomer or polymer comprising:

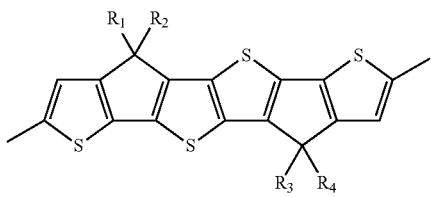

wherein R1, R2, R3, and R4 are independently hydrogen or solubilizing groups.

In one embodiment, $R_1$, $R_2$, $R_3$, and $R_4$ are the same group. In one embodiment, $R_1$, $R_2$, $R_3$, and $R_4$ are the same group and comprise an aromatic group. In one embodiment, $R_1$, $R_2$, $R_3$, and $R_4$ are the same group and comprise an arylalkyl group. In one embodiment, $R_1$, $R_2$, $R_3$, and $R_4$ are the same group and are a $C_1$-$C_{25}$ group. In one embodiment, the polymer is present having a molecular weight of at least 10,000 number average molecular weight. In one embodiment, the oligomer or polymer is a donor-acceptor oligomer or polymer. In one embodiment, the oligomer or polymer is a donor-acceptor polymer, and has at least two types of donors, or at least two types of acceptors. In one embodiment, the oligomer or polymer is soluble in chloroform, chlorobenzene, dichlorobenzene, or trichlorobenzene. In one embodiment, polymer is present and has a molecular weight of at least 10,000 number average molecular weight and is soluble in chloroform, chlorobenzene, dichlorobenzene, or trichlorobenzene.

Another embodiment provides at least one oligomer or polymer comprising at least one repeat unit comprising:

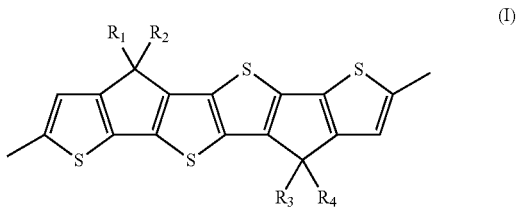

wherein $R_1$, $R_2$, $R_3$, and $R_4$ are, optionally, the same group and are a $C_1$-$C_{25}$ group.

A monomer is also provided to provide the repeat unit in (I), wherein the monomer can comprise a structure (II):

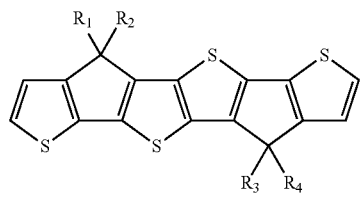

wherein the end terminal rings are adapted for polymerization, and wherein $R_1$, $R_2$, $R_3$, and $R_4$ an embodiment as described herein.

For example, in one embodiment, $R_1$, $R_2$, $R_3$, and $R_4$ are the same group. In one embodiment, $R_1$, $R_2$, $R_3$, and $R_4$ are the same group and comprise an aromatic group. In one embodiment, $R_1$, $R_2$, $R_3$, and $R_4$ are the same group and comprise an arylalkyl group. In one embodiment, $R_1$, $R_2$, $R_3$, and $R_4$ are the same group and are a $C_1$-$C_{25}$ group. In one embodiment, the monomer is functionalized with electrophilic groups for polymerization. In one embodiment, the monomer is functionalized with nucleophilic groups for polymerization. In one embodiment, the monomer is functionalized with groups comprising metal, such as for example tin, for polymerization. In one embodiment, the monomer is functionalized for cross coupling polymerization, including palladium cross coupling polymerization. In one embodiment, the monomer is functionalized for Ullman, Yamamoto, or Suzuki polymerization. In one embodiment, the terminal thiophene rings are functionalized for polymerization. The monomer can be used with one or more other comonomers to form polymers comprising (I).

Another embodiment provides an ink composition comprising at least one oligomer, or polymer comprising:

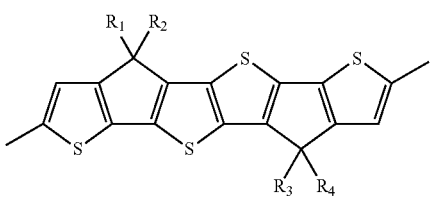

wherein R1, R2, R3, and R4 are independently hydrogen or solubilizing groups; and at least one solvent.

In one embodiment, $R_1$, $R_2$, $R_3$, and $R_4$ are the same group. In one embodiment, $R_1$, $R_2$, $R_3$, and $R_4$ are the same group and comprise an aromatic group. In one embodiment, $R_1$, $R_2$, $R_3$, and $R_4$ are the same group and comprise an arylalkyl group. In one embodiment, $R_1$, $R_2$, $R_3$, and $R_4$ are the same group and are a $C_1$-$C_{25}$ group. In one embodiment, the oligomer or polymer is a polymer having a molecular weight of at least 10,000 number average molecular weight. In one embodiment, the oligomer or polymer is a donor-acceptor oligomer or polymer. In one embodiment, the oligomer or polymer is a donor-acceptor polymer, and has at least two types of donors, or at least two types of acceptors. In one embodiment, the solvent comprises at least two solvents, optionally halogenated solvents, and the ink composition further comprises at least one additive. In one embodiment, the solvent comprises a mixture comprising at least orthodichlorobenzene and trichlorobenzene.

Another embodiment provides an OPV device comprising at least one OPV active layer comprising at least one polymer comprising:

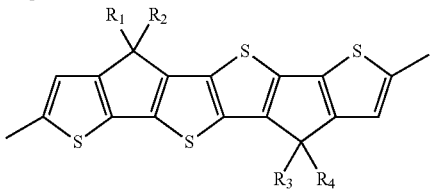

wherein $R_1$, $R_2$, $R_3$, and $R_4$ are independently hydrogen or solubilizing groups.

In one embodiment, $R_1$, $R_2$, $R_3$, and $R_4$ are the same group. In one embodiment, $R_1$, $R_2$, $R_3$, and $R_4$ are the same group and comprise an aromatic group. In one embodiment, $R_1$, $R_2$, $R_3$, and $R_4$ are the same group and comprise an arylalkyl group. In one embodiment, $R_1$, $R_2$, $R_3$, and $R_4$ are the same group and are a $C_1$-$C_{25}$ group. In one embodiment, the polymer has a molecular weight of at least 10,000 number average molecular weight. In one embodiment, the polymer is a donor-acceptor polymer. In one embodiment, the polymer is a donor-acceptor polymer, and has at least two types of donors, or at least two types of acceptors. In one embodiment, the device comprises at least one polythiophene a hole transport layer. In one embodiment, the active layer further comprises at least one n-type material.

Another embodiment provides a coated substrate comprising at least one substrate and at least one coating, wherein the coating comprises at least one polymer comprising:

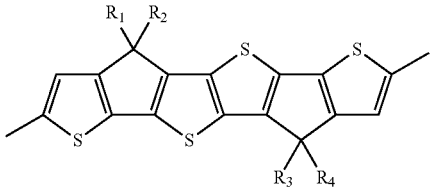

wherein $R_1$, $R_2$, $R_3$, and $R_4$ are independently hydrogen or solubilizing groups.

In one embodiment, $R_1$, $R_2$, $R_3$, and $R_4$ are the same group. In one embodiment, $R_1$, $R_2$, $R_3$, and $R_4$ are the same group and comprise an aromatic group. In one embodiment, $R_1$, $R_2$, $R_3$, and $R_4$ are the same group and comprise an arylalkyl group. In one embodiment, $R_1$, $R_2$, $R_3$, and $R_4$ are the same group and are a $C_1$-$C_{25}$ group. In one embodiment, the polymer has a molecular weight of at least 10,000 number average molecular weight. In one embodiment, the polymer is a donor-acceptor polymer. In one embodiment, the polymer is a donor-acceptor polymer, and has at least two types of donors, or at least two types of acceptors. In one embodiment, the substrate is a flexible substrate. In one embodiment, the substrate comprises a hole transporting layer next to the coating.

Another embodiment provides a method comprising: functionalize at least one thieno[3,2-b]thiophene compound with two reactive functional groups, one reactive group on each thiophene ring to provide a compound I; provide at least one thiophene compound comprising a leaving group at the 2-position and a carboxylate at the 3-position to provide a compound II; react compound I and compound II to produce compound III which is a compound comprising a central thieno[3,2-b]thiophene moiety linked to opposing thiophene rings; react compound III so that carboxylate groups are converted to hydroxyl groups to provide compound IV; react compound IV in a ring closure reaction to provide at least one compound represented by (II) which is compound V:

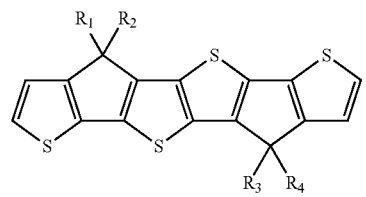

optionally, functionalize compound V to have two polymerization groups and provide compound VI. In one embodiment, the optional functionalization step to provide compound VI is carried out. The R groups in (II) can be R1, R2, R3, or R4 as in (I).

Another embodiment provides a method comprising: providing a monomer comprising a moiety represented by:

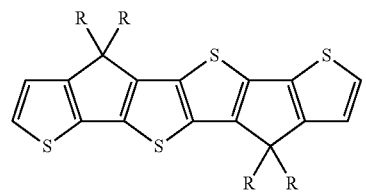

wherein $R_1$, $R_2$, $R_3$, and $R_4$ are independently hydrogen or solubilizing groups; and polymerizing the monomer.

Another embodiment provides a composition comprising at least one donor-acceptor polymer comprising:

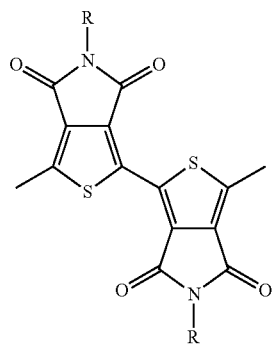

wherein R is a solubilizing group, and wherein the polymer further comprises

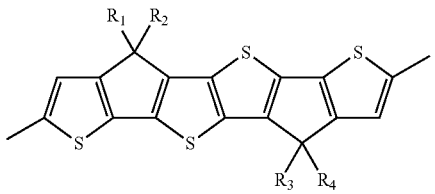

wherein $R_1$, $R_2$, $R_3$, and $R_4$ are independently hydrogen or solubilizing groups.

At least one advantage for at least one embodiment is ability to make high mobility polymers.

At least one additional advantage for at least one embodiment is to have relatively high efficiency photovoltaic devices.

At least one additional advantage is ability to solubilize the polymers via four side groups R1-R4.

At least one additional advantage for at least one embodiment is to have polymers with bathochromic absorption profiles and sharp band edges.

At least one additional advantage is ability to control the HOMO to a desired level (e.g., weaker donor) so good matching can occur between donor(s) and acceptor(s).

BRIEF DESCRIPTION OF THE DRAWINGS

FIG. 3 illustrates external quantum efficiency (eqe) data for several polymers.

DETAILED DESCRIPTION

Introduction

Figure 1:
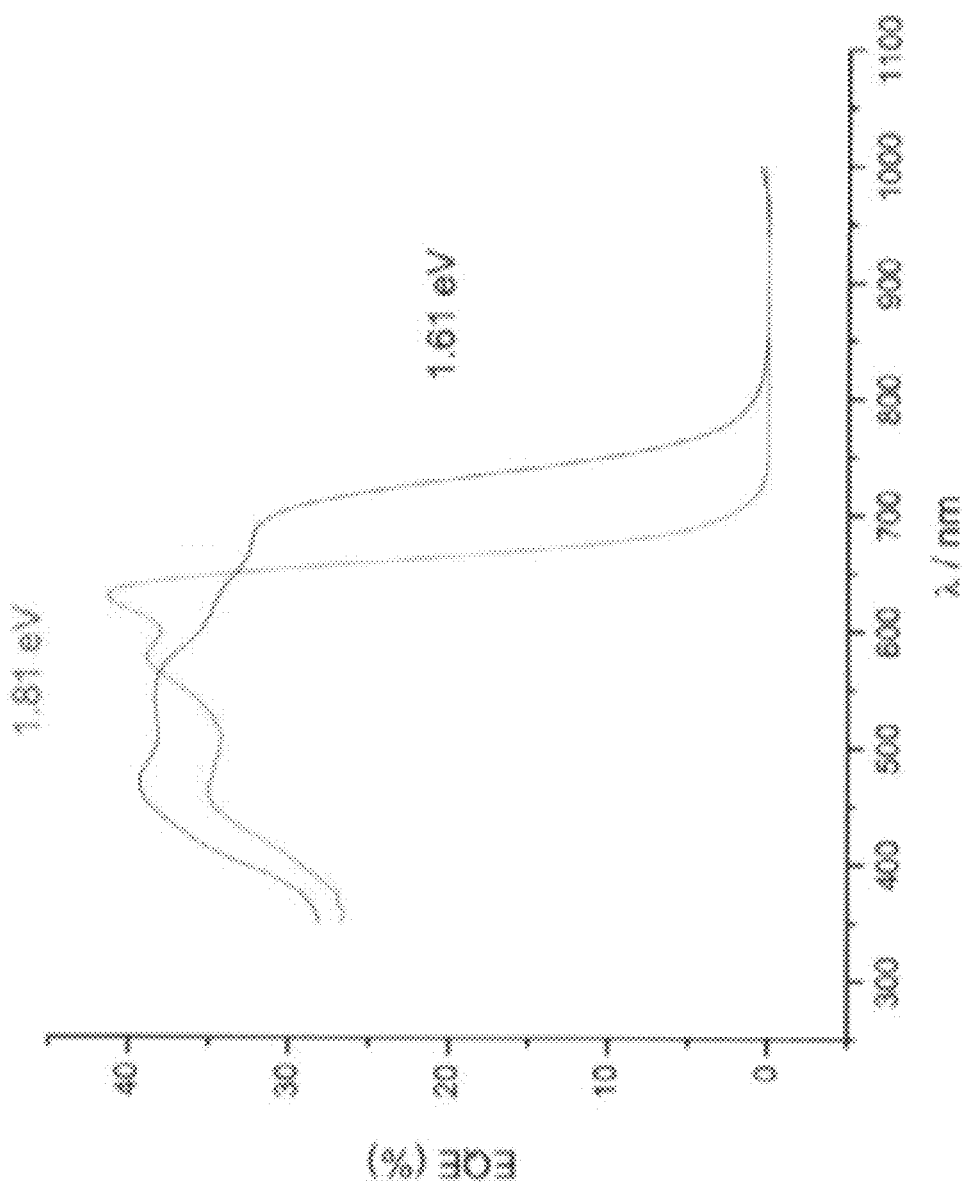
FIG. 1 illustrates external quantum efficiency (eqe) data for several polymers.

All references cited herein are incorporated by reference in their entirety.

Priority U.S. regular application Ser. No. 12/874,163 filed Sep. 1, 2010 is hereby incorporated by reference in its entirety.

U.S. regular application Ser. No. 12/874,137 filed Sep. 1, 2010 is hereby incorporated by reference in its entirety.

U.S. regular application Ser. No. 12/828,121 filed Jun. 30, 2010 is hereby incorporated by reference in its entirety.

U.S. regular application Ser. No. 12/371,556 filed Feb. 13, 2009 is hereby incorporated by reference in its entirety.

PCT applications serial nos. PCT/US2010/037802 and PCT/US2010/037805, each filed Jun. 8, 2010, are hereby incorporated by reference in their entireties.

Low band gap materials are known in the art. See, for example, Blouin et al., *Accounts of Chemical Research*, 1110-1119, September 2008, 41, 9.

Polymer solar cells are known in the art. See, for example, Chen et al., *Advanced Materials*, 2009, 21, 1-16; Hoppe, *Adv. Polym. Sci.*, 2008, 214, 1-86; Gunes et al., *Chem. Rev.*, 2007, 107, 1324-1338. See also, for example, organic photovoltaic technologies described in, for example, a series of articles in *Accounts of Chemical Research*, 42, 11 Nov. 2009, including Zhu et al. (1779-1787); Bredas et al. (1691-1699); Chen et al. (1709-1718); Heremans et al. (1740-1747); Nelson et al. (1768-1778); Peet et al. (1700-1708); Potscavage et al. (1758-1767); Roncali (1719-1730).

Organic semiconductors including arylamines and TPD are known in the art. See, for example, Walzer et al., *Chem. Rev.*, 2007, 107, 1233-1271.

One exemplary embodiment provides compositions comprising at least one conjugated copolymer, wherein the copolymer backbone comprises at least one donor moiety and at least one acceptor moiety, and wherein the copolymer has at least two high extinction coefficient chromophores thereby covering the high photon flux portion of the solar spectrum which is from about 400-1000 nm and centered at about 750-800 nm. Broad absorption is desired including up to the near-infrared region. Vibronic structure can be detected.

For all structures shown herein, for monomers, oligomers, and polymers, the side groups can be adapted to be solubilizing groups as described further herein.

An oligomer can have a number of repeat units of six or less.

PART ONE: POLYMERS, OLIGOMERS, MONOMERS

One embodiment provides an oligomer or polymer comprising:

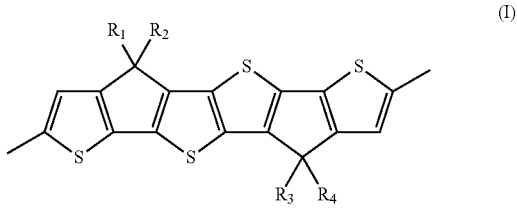

(I)

wherein $R_1$, $R_2$, $R_3$, and $R_4$ are independently hydrogen or solubilizing groups.

An important aspect of oligomers and polymers which comprise (I) is that they are sufficiently soluble so that inks can be formed and solution processing can be achieved. Solubility can be examined in organic or aqueous solvents. One skilled in the art can adapt the R group and other parts of the polymer chain and side groups, as well as molecular weight, to generate sufficient solubility. Organic solvents can be, for example, halogenated and non-halogenated solvents. The solvent can be a single solvent or a mixture of solvents. An example of halogenated solvent is ortho-dichlorobenzene, and this solvent can be used to measure solubility. Solubility can be measured at 25° C. Solubility can be, for example, at least 1 mg/mL, or at least 20 mg/mL. In some embodiments, solubility can be adapted to provide good bulk heterojunction (BHJ) layer morphology. Higher molecular weight may be preferred to modulate solubility, and molecular weight can be used with other formulation strategies including additives to modulate solubility and/or BHJ formation. In addition, polymers can be both soluble and also functionally dispersible in a solvent so that solution processing can be achieved, whether or not a true solution is formed.

The R groups in (I) can be adapted to facilitate or provide solubility. The R groups can also be adapted to provide desired electronic properties. The R groups can be also adapted to provide steric and molecular stacking properties.

The atom in the R groups bonding to the polymer chain can be, for example, carbon.

For example, the R groups can be optionally substituted alkyl, optionally substituted linear alkyl, optionally substituted branched alkyl, optionally substituted aryl, optionally substituted alkylaryl, optionally substituted arylalkyl, optionally substituted alkoxy, or optionally substituted aryloxy. The R group can have, for example, 3-30 carbons, or 4-25 carbons, or 5-15 carbons. Examples include butyl, octyl and dodecyl, as well as ethylhexyl. Different R groups can be used in the same polymer as needed. The R group can be chiral. The R group can be functionalized or substituted as desired. Examples of substituents include amino, carboxylic acid, ester, halogen (including fluoro and chloro), pseudohalogen (e.g., cyano), and other functional groups known in the art.

The R groups can comprise a heteroatom, such as oxygen or nitrogen in the carbon chain (e.g., ether or amino linkages, respectively). The R group can comprise C1-C20 alkoxy, or C1-C20 alkyleneoxy, for example. The R group can be an oligoether, such as, for example, alkoxyalkoxy or alkoxyalkoxyalkoxy, such as, for example, methoxyethoxyethoxy.

The polymer comprising structure (I) can be free of protecting groups, and in particular the R groups can be free of protecting groups.

The R groups can be adapted to modulate or tune the LUMO, including provide a decreasing or increasing LUMO, or provide better solid state packing, or provide improved charge transport, and/or provide environmental stability. For example, the R group can be halogenated including comprise a group comprising chlorine or fluorine. The R group can be, for example, perfluorinated. The R group can be, for example, a perfluoroalkyl group such as, for example, —$C_3F_7$. The R group can be, for example, a perfluoroarylgroup, such as, for example, —$C_6F_5$. For use of halogenated substituent groups to modulate LUMO and solid state packing, see, for example, Schmidt et al., *J. Am. Chem. Soc.,* 2009, 131, 6215-6228.

A particular oligomer or polymer could comprise two or more different structures (I).

Polymer comprising (I) can be a random copolymer or a regular alternating copolymer. Polymer comprising (I) can comprise multiple repeat moieties.

Moieties in the polymer chain can provide for carbon-carbon bonding with conjugation, and, in addition, can provide charge transport.

Polymer side groups can provide electron withdrawing or electron accepting character, and the strength of this can be varied, e.g., weak or strong, or from weak to strong. Push-pull electronic effects can be produced. Electron donating side groups can be also used as appropriate.

Polymer side groups can be protected or deprotected. For example, butyloxycarbonyl (BOC) can be used to protect amino side groups. However, an embodiment comprises the polymer being totally free of protecting groups.

Block copolymers can be prepared. Either all blocks can be embodiments as described herein, or only a subset of block(s) can be embodiments described herein. For example, a block copolymer could comprise both a conjugated polymer block and a non-conjugated polymer block, or both a donor-acceptor block, and a non-donor-acceptor block. Also, block copolymers can be prepared comprising blocks of different donors and acceptors, e.g., (D1-A1)-b-(D1-A2), and the like.

In one embodiment, the polymer comprises a number average molecular weight, Mn, of at least 6,000 g/mol, or of at least 7,500 g/mol, or at least 10,000. In another embodiment, the polymer comprises a number average molecular weight, Mn, of at least 20,000, or at least 30,000, or at least 40,000, or at least 50,000.

In particularly preferred examples, $R_1$, $R_2$, $R_3$, and $R_4$ can be, independently, $C_1$-$C_{25}$ optionally substituted alkyl, aryl, alkylaryl, or arylalkyl. Examples include phenyl, wherein the phenyl is optionally further substituted at the 4 position with, for example, an alkyl group such as, for example, a branched group such as, for example, ethylhexyl. In one embodiment, the R groups in (I) are the same.

A monomer is also provided to provide this repeat unit (I). The monomer can comprise, for example, structure (II) which can be adapted to have two or more functional groups for polymerization through the terminal rings:

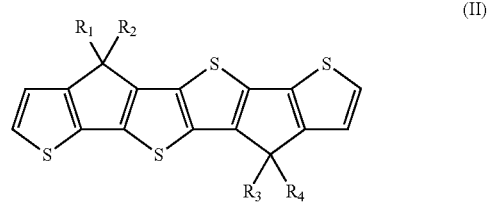

The R groups shown in (II) can be as described for the R groups in structure (I).

The oligomer or polymer comprise one or more of the repeat unit (I).

The oligomer or polymer can comprise a donor-acceptor structure. Structure (I) can be a donor. The polymer can comprise one or more donors, including (I), and/or one or more acceptors. The polymer can comprise only two donors and acceptors, or only three donors and acceptors, or at least two or at least three donors and acceptors. The R groups can be selected to provide a higher amount of symmetry.

Particular examples of polymers include:

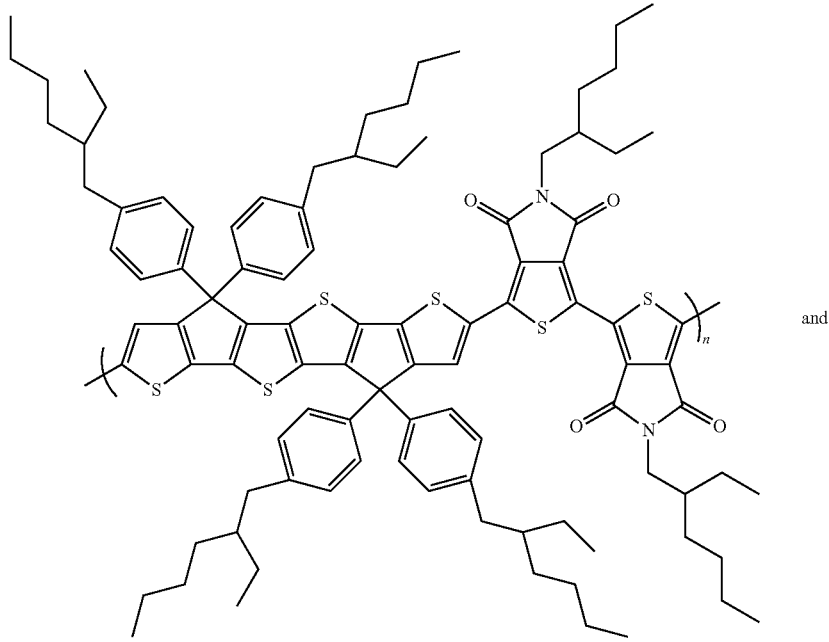

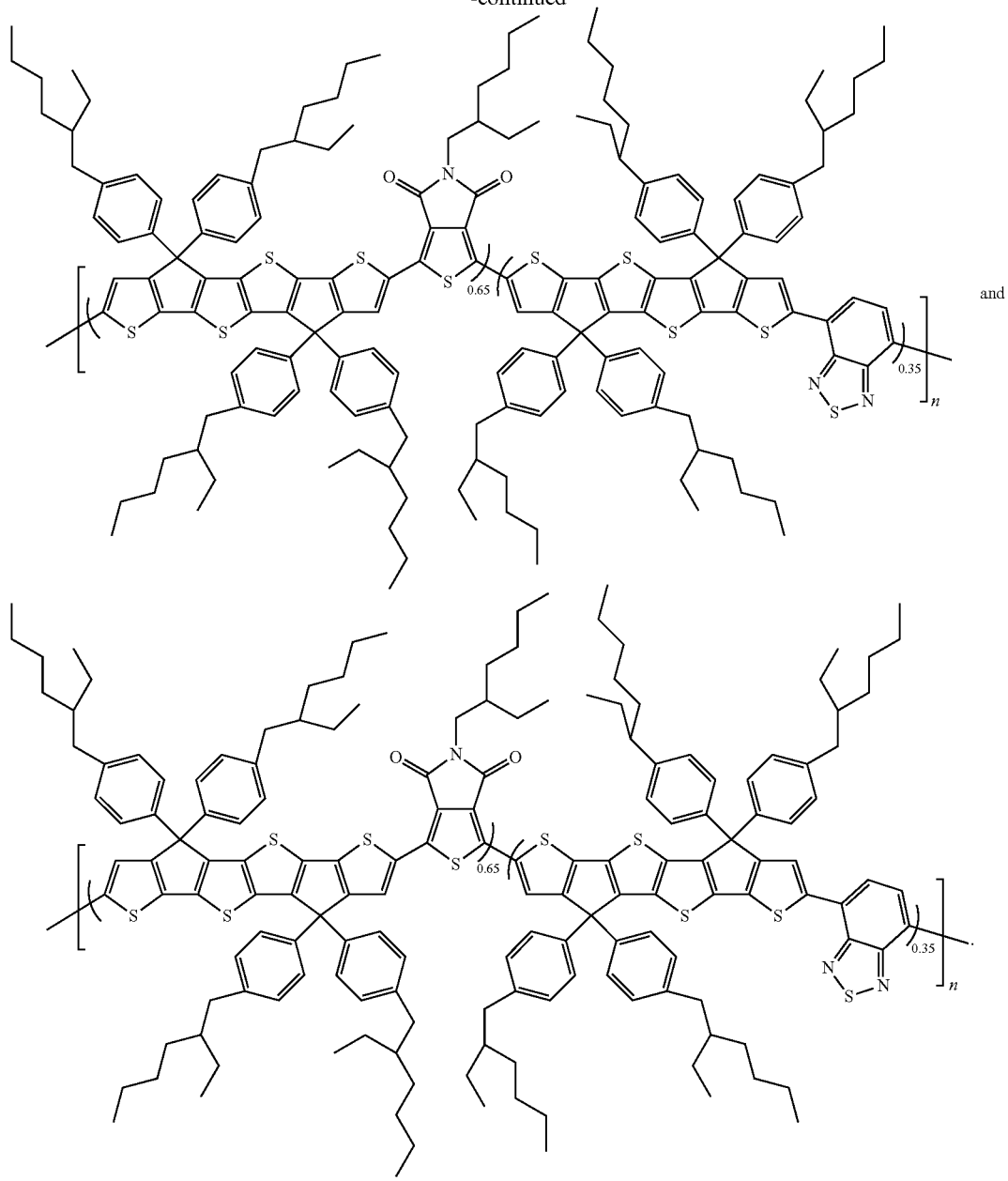

Other examples of polymer structures, including donor acceptor polymers, comprising (I) are shown in the Appendix A. The side groups in the polymers of Appendix A can be tailored for solubility, stacking and morphology, and electronic interactions.

Silole

In addition, monomers, oligomers, and polymers can be prepared with comprise a silole moiety represented by (III):

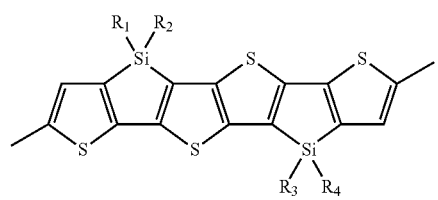
(IIIA)

wherein $R_1$, $R_2$, $R_3$, and $R_4$ are independently hydrogen or solubilizing groups. For example, $R_1$, $R_2$, $R_3$, and $R_4$ can be, independently, $C_1$-$C_{25}$ optionally substituted alkyl, aryl, alkylaryl, or arylalkyl. Examples include phenyl, wherein the phenyl is optionally further substituted at the 4 position with, for example, an alkyl group such as, for example, a branched group such as, for example, ethylhexyl. In one embodiment, the R groups in (I) are the same.

The silole structure can be also shown as in (IIIB) where the linkages into the polymer chain are not shown at the end:

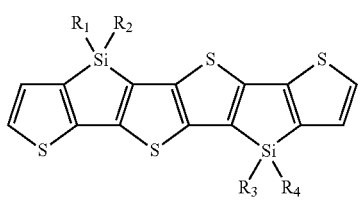
(IIIB)

The terminal thiophene rings can be adapted to include functionalities for polymerization.

More generally, the structure can be:

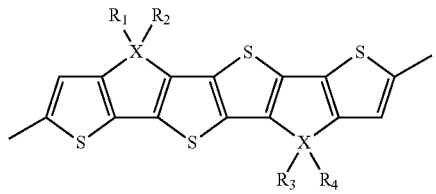

where X is C or Si for example.

Donors and other Acceptors

In addition to structure (I), a variety of donors, or donor moieties, are known in the art. Appendix B illustrates an exemplary listing of donor structures which can be used. The structures shown in Appendix B can be used in monomers, dimers, trimers, oligomers, and polymers. The side group can be varied and is not limited by side groups shown structure in Appendix B. For example, the side groups in the donor structures of Appendix B can be tailored for solubility, stacking and morphology, and electronic interactions. In Appendix B, the representation of —R or R— means a linkage site for a reactive group, or a linkage site for linking into another moiety like a dimer, trimer, oligomer, or polymer. Illustration of two of these sites means the moiety can be bivalently linked to another moiety including a polymer chain.

In addition, a variety of acceptors, or acceptor moieties, can be used. Examples include but are not limited to those shown in Appendix C. The structures shown in Appendix C can be used in monomers, dimers, trimers, oligomers, and polymers. The side group can be varied and is not limited by shown structure in Appendix C. For example, the side groups in the structures of Appendix C can be tailored for solubility, stacking and morphology, and electronic interactions. In Appendix C, the representation of —R or R— means a linkage site for a reactive group, or a linkage site for, after reaction, linking into another moiety like a dimer, trimer, oligomer, or polymer. Two of these sites means the moiety can be bivalently linked to another moiety including a polymer chain.

Acceptors are particularly important if they have one or more carbonyl groups which can interact with a thiophene ring in (I).

An example of an acceptor is the diketopyrroleopyrrole-based acceptor moiety. See, for example, Zhou et al., *Chemistry of Materials*, 2009, "Synthesis and Photovoltaic Properties of Diketopyrrolopyrrole-Based Donor-Acceptor Complexes."

For a single polymer, more than one donor can be used: e.g., D1, D2, D3, and the like. In addition, for a single polymer, more than one acceptor can be used: e.g., A1, A2, A3, and the like.

Polymers can comprise D1-A1 moieties, D2-A2 moieties, D3-A3 moieties, and the like, as well as their intermixed moieties, such as, for example, D1-A2, and the like.

Use of more than one donor or acceptor can provide broader and/or stronger absorption bands and/or vibronic structures.

Spacer moieties can be used as desired.

Embodiments for Copolymer Architecture Based on D1, D2, A1, and A2

The following chart shows different, exemplary embodiments for copolymer architecture with different donors, D1 and D2 donors, and different acceptors, A1 and A2 acceptors. The Chart I shows examples which are different from the -[D-A]-alternating formula seen in the prior art.

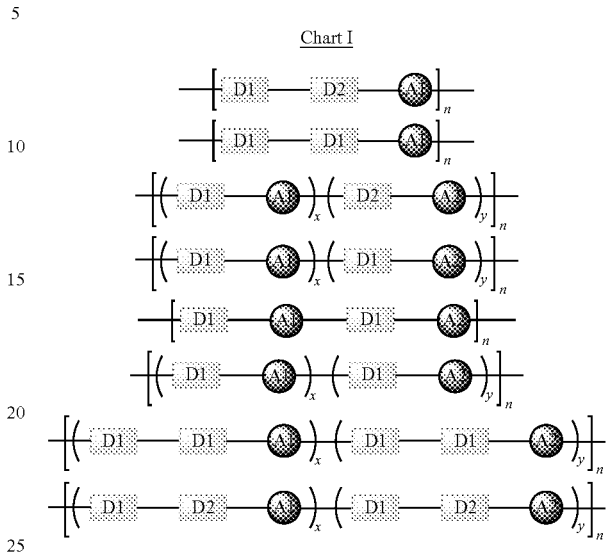

Chart I

The acceptors, A1, A2, or both can comprise the acceptors listed in Appendix C.

The donors can be selected from the structure (I) and those listed in Appendix B, for example.

The structures shown in Chart I can be extended to further include additional donors, e.g., D3, D4, D5, and the like, or additional acceptors, e.g., A3, A4, A5, or the like.

Ratio of Donor and Acceptor

The molar ratio of donor and acceptor can be one, less than one, or more than one. In calculating this ratio, there can be a single donor and/or a single acceptor, or there can be more than one donor and/or more than one acceptor. In other words, the polymer does not need to comprise equal molar amounts of donor and acceptor. The polymer can comprise more donor than acceptor, or more acceptor than donor. Chart I shows examples of this. For example, the ratio can be 2:1. Also, the ratio of different donors and acceptors within the polymer does not need to comprise equal molar amounts, e.g., the total ratio of donor and acceptor moieties in the polymer can be one where donor comprises a sum of different ratios of D1 and D2, and the like, and/or acceptor comprises a sum of different ratios of A1, A2, and the like. In other words, the ratio of the molar amounts of D1 and D2 does not have to be one, and the ratio of the molar amounts of A1 and A2 does not have to be one.

Random or Alternating Copolymers

Different copolymer microstructures can be prepared as known to those skilled in the polymer chemistry arts. For example, random copolymer structures can be produced. Mixed monomer polymerization can be carried out. Non-random copolymer structures can be produced.

For the random copolymer embodiment, one can use an appropriate synthetic sequence to obtain good materials. Synthetic approaches include, for example, Kumada, Suzuki, Negishi or Stille couplings for polymerization. See, for example (a) *Cross-Coupling Reactions: A Practical Guide*, Ed. Miyaura, 2002; (b) *Handbook of Organopalladium Chemistry for Organic Synthesis*, Ed. Negishi, 2002; (c) Kuwano et al., *J. Org. Chem.*, 2002, 67, 6479-6486; (d) Yu et al. *J. Am. Chem. Soc.* 2009, 131, 56; (e) Hou et al., *Macromolecules*, 2008, 41 (16), 6012-6018; (f) Blouin et al., *J. Am.*

Chem. Soc. 2008 130 (2), 732-742; (g) Swager et al. *Adv. Mater.* 2001, 13, 1775; (h) Koeckelberghs et al. *Macromolecules.* 2007, 40, 4173; (i) *High-Efficient-Low-Cost Photovoltaics,* Springer Verlag Berlin Heidelberg, 2009, Eds: Petrova-Kock, V.; Goetzberger, A., 195-222. Also, Ullman and Yamamoto coupling or polymerization can be used.

One embodiment provides for preparing high purity intermediates, such as trimers.

Regular alternating copolymer structures can be produced. Chart I shows examples of this.

Polymer Properties/Chromophore/Absorption Spectra

Polymer properties can be adapted to provide the good photovoltaic properties and to follow the design rules noted herein.

Lambda max can be, for example, greater than 600 nm.

Absorption edge can be extended into the red region. The absorption edge can comprise a sharp edge.

Absorption spectra are important parameters for the polymers, particularly for photovoltaic applications. It is known to record absorption spectra, including UV-Vis absorption spectra, for conjugated polymers. See, for example, Brown et al., *Phys. Rev. B,* 67, 064203 (2003) (describing spectra for different kinds of polythiophenes).

Intramolecular Non-Covalent Interactions Including Carbonyl Interaction with Thiophene Sulfur A variety of intramolecular non-covalent interactions, such as electrostatic, coulombic, hydrogen bonding or chelates can be used to provide increased rigidity and/or planarity to the polymer chain and its chromophores, although various embodiments described herein are not necessarily limited by theory. Increased rigidity can be used to increase the likelihood for a well behaved excited state and lead to good excitonic diffusion distances and minimization of energy loss pathways from excited state (e.g., charge trapping, polaronic quenching, excited state deactivation, or even localization). Absorption profiling can be used to examine such features.

In particular, while various embodiments described herein are not necessarily limited by theory, it is believed that for at least some embodiments, when a thiophene ring such as the terminal thiophene rings in (I) is covalently linked to a moiety which has appropriately spaced carbonyl groups, the carbonyl groups can interact with thiophene sulfur. The carbonyl oxygen is negatively charged compared to the thiophene sulfur which is relatively positively charged. This can provide planarization and/or increase rigidity in the backbone and improve performance. The interactions can be measured by methods known in the art including, for example, x-ray or NOE (Nuclear Overhauser Effect). See, for example, Pomerantz et al., *Synthetic Metals,* 2003, 135-136, 257-258; Pomerantz et al., *Tetrahedron Letters,* 2003, 44(8), 1563-1565; and Pomerantz et al., *Tetrahedron Letters,* 40, 1999, 3317-3320. Also, for sulfur-oxygen interactions, see, for example, Turbiez et al., *Chem.-Eur. J.* 2005, 11, 3742-3752.; and Apperloo et al., J. L. *Chem.-Eur. J.* 2002, 8, 2384-2396.

Donor-Acceptor polymers comprising diketo types of structures, such as dioxypyrrolo-functionality, can provide intramolecular interactions as a "design rule" for the synthesis of new materials for application in organic electronics, such as OPVs, achieving unexpected performances.

The thiophene ring can be part of an isolated thiophene moiety or a fused ring thiophene moiety such as the thiophene found in (I) or in benzodithiophene.

Other embodiment relate to methods of making the monomers, oligomers, and polymers.

Monomers and polymerizations for monomers comprising (I) or (II) can be carried out including the embodiments shown in the working examples.

For example, one embodiment provides a method comprising:

(a) In a first step, functionalize at least one thieno[3,2-b]thiophene compound with two reactive functional groups, one reactive group on each thiophene ring to provide a compound I. Example 1 in the working examples provides an example of this step. For example, reactive functional groups can be, for example, trimethyltin.

(b) In another step, provide at least one thiophene compound comprising a leaving group at the 2-position and a carboxylate at the 3-position to provide a compound II. Example 2 in the working examples provides an example of this step. A carboxylic acid moiety can be converted to a carboxylate moiety.

(c) In another step, react compound I and compound II to produce compound III which is a compound comprising a central thieno[3,2-b]thiophene moiety linked to opposing thiophene rings. Example 3 in the working examples provides an example of this step.

(d) In another step, react compound III so that carboxylate groups are converted to hydroxyl groups to provide compound IV. Example 4 in the working examples provides an example of this step.

(e) In another step, react compound IV in a ring closure reaction to provide at least one compound represented by (II) which is compound V:

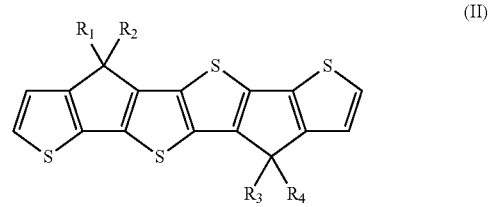

(II)

Example 5 in the working examples provides an example of this step.

(f) Optionally, in a subsequent step, functionalize compound V to have two polymerization groups and provide compound VI. Example 6 in the working examples provides an example of this step. In one embodiment, the optional functionalization step to provide compound VI is carried out.

PART II: USES, INKS, AND DEVICES

The materials, monomers, dimers, trimers, oligomers, polymers, and copolymers described herein in Part I, the working examples, and claims, can be used in organic electronic devices including, for example, OLEDs, OPVs including as OPV active layer, transistors, OFETs, batteries, and printed electronics generally, as well as sensors. The methods described in Part II can be adapted for the particular compounds and polymers being used.

For example, photovoltaic cells (solar cells) are known in the art. See, for example, Sun and Sariciftci, *Organic Photovoltaics, Mechanisms, Materials, and Devices,* 2005. The photovoltaic cell can comprise an active layer comprising a composition comprising at least one p-type material and at least one n-type material. One can engineer HOMO, LUMO, and band gaps for the p- and n-type materials for good performance. The morphology of the active layer can be adapted to provide good performance. For example, a nanoscale morphology can be prepared. An example is a bulk heterojunction. Bilayers can be made as described in, for example, Ayzner et al., *J. Phys. Chem. C.*, 2009, 113, 20050-20060 (e.g., describing all solution-processed bilayers in solar cells).

The photovoltaic device can comprise at least one cathode, at least one anode, and at least one photovoltaic active layer disposed between the cathode and anode. The active layer can comprise a p-type material and an n-type material.

In an OPV active layer, the polymers described herein, which can be a p-type material, can be combined with n-type materials or acceptor moieties, such as, for example, fullerenes and fullerene derivatives. An example of a fullerene derivative is PCBM. Fullerenes can be also derivatized, as described in, for example, PCT Patent Publication WO 2008/018931 filed May 2, 2007 and US Patent Publication 2008/0319207 published Dec. 25, 2008, both to Laird, et al. (Plextronics, Inc.). Other types of n-type materials known in the art can be used. If desired, larger area photovoltaics can be fabricated. See, for example, Bundgaard et al., *Solar Energy Materials and Solar Cells*, 2007, 91, 1019-1025.

Polymer solar cells, including polymer fullerene solar cells, are described in, for example, Hoppe et al., *Adv. Polym. Sci.* (2008), 214: 1-86; Zhu et al., "Design Rules for Efficient Organic Solar Cells," Chapter 13, 195-222 in *High-Efficient Low-Cost Photovoltaics*, Springer, 2009.

OLED devices are known in the art including white OLEDs, or WOLEDs. See, for example, Li and Meng, *Organic Light Emitting Materials and Devices*, CRC Taylor, 2006 and US Patent Publication 2006/0078761 published Apr. 13, 2006. The devices can comprise, for example, multi-layer structures including, for example, an anode, including a transparent conductor, such as a transparent conductive oxide (TCO) on glass or PET or PEN; a hole injection layer; an electroluminescent layer, such as a polymer layer; a conditioning layer, such as LiF, and a cathode, such as for example Ca, Al, or Ba.

Methods known in the art can be used to fabricate organic electronic devices including for example OLED devices. Methods known in the art can be used to measure brightness, efficiency, and lifetimes. OLED patents include for example U.S. Pat. Nos. 4,356,429 and 4,539,507 (Kodak). Conducting polymers which emit light are described in for example U.S. Pat. Nos. 5,247,190 and 5,401,827 (Cambridge Display Technologies). See also Kraft et al., "Electroluminescent Conjugated Polymers—Seeing Polymers in a New Light," *Angew. Chem. Int. Ed.*, 1998, 37, 402-428, including device architecture, physical principles, solution processing, multilayering, blends, and materials synthesis and formulation, which is hereby incorporated by reference in its entirety.

In addition, printed electronics are generally known in the art. See, for example, *Printed Organic and Molecular Electronics*, Ed. D. Gamota et al., 2004. For example, Chapters 1 and 2 describe organic semiconductors, Chapter 3 describes manufacturing platforms for printing circuits, Chapter 4 describes electrical behavior of transistors and circuits, Chapter 5 describes applications, and Chapter 6 describes molecular electronics. See also Pope et al., *Electronic Processes in Organic Crystals and Polymers*, 1999.

Solutions and Ink Formulations

The materials, polymers, and copolymers can be put into solution or dispersion form, including ink formulations, for further processing, adapting to the particular application at hand including electronic devices and organic electronic devices, such as, for example, OLED, solar cells and active layers of solar cells.

Lower cost electronic devices can be enabled because polymers, such as those described herein, can be processed into inks which can then be handled in the same manner as inks in conventional printing processes. Ink compositions used for forming, for example, the active layer of an organic photovoltaic device can be made by dissolving p-type and n-type materials in a solvent system, optionally containing other additives.

The solvents and conjugated polymer inks can be formulated or adapted for use in a particular application, such as a solar cell that may include additional additives, such as electron acceptors. The additive(s) and solvents can be adapted to provide good dispersability of the n- and p-type materials, solubility of the n- and p-type materials, and stability of the ink formulation. For example, solvents can be used which provide good solubility or dispersability for fullerenes or fullerene derivative n-type compounds. Solvents can be adapted to be environmentally friendly in view of regulations, and can be, for example, halogen free. In other embodiments additives can be included in the ink that can improve the final film morphology or other properties. For example, solvent additives disclosed in US Patent Publication entitled "Processing Additives for Fabricating Organic Photovoltaic Cells" 2009/0108255 to Bazan et al., published on Apr. 30, 2009 can be included.

Solvent(s) and solvent additive(s) can be removed from the ink compositions, and films can be formed. Solid films can be formed that either comprise solvent(s) and solvent additive(s), are substantially free of solvent(s) and solvent additive(s), or are free of solvent(s) and solvent additive(s). For example, the amount of remaining solvent can be less than about 5% by weight, or less than about 1% by weight, or less than about 0.1% by weight. For example, the amount of remaining solvent additive can be less than about 5% by weight, or less than about 1% by weight, or less than about 0.1% by weight.

Conventional methods can be used to cast polymer materials from the compositions to provide solid forms, including thin film forms and printed forms. For example, the p-type and n-type polymers of the active layer can be dissolved in the solvent to form an ink, and then allowed to dry. Suitable coating methods are known. These include roll-to-roll coating, screen printing, spin casting, spin coating, doctor blading, dip coating, spray coating, or ink jet printing, and other known coating and printing methods.

Ink Components

Ink components known in the art can be used including, for example, solvents and n-type materials. The amounts of the components can be adapted to improve performance.

N-Type Materials

The active layer composition in, for example, a solar cell may include an n-type component or electron acceptor, or an electron acceptor moiety. These can be materials with a strong electron affinity and good electron accepting character. The n-type component should provide fast transfer, good stability, and good processability. The n-type material is desirably soluble in, dispersible in, or otherwise miscible with the solvents in order to provide for solution processing. The n-type component may take the form of particles, including microparticles and nanoparticles, inorganic particles, organic particles, and/or semiconductor particles.

For example, the active layer can comprise an n-type material comprising at least one fullerene structure. Fullerenes are known in the art. Fullerenes can be described as spheroidal carbon compounds. For example, the fullerene surface can present [6,6] bonding and [6,5] bonding as known in the art. The fullerene can have a surface comprising six-membered and five-membered rings. Fullerenes can be for example C60, C70, or C84, and additional carbon atoms can be added via derivative groups. See for example Hirsch, A.; Brettreich, M.,

*Fullerenes: Chemistry and Reactions*, Wiley-VCH Verlag, Weinheim, 2005, which is hereby incorporated by reference including teachings for fullerene nomenclature and synthesis, derivatization, reduction reactions (Chapter 2), nucleophilic additions (Chapter 3), cycloadditions (Chapter 4), hydrogenation (Chapter 5), radical additions (Chapter 6), transition metal complex formation (Chapter 7), oxidation and reactions with electrophiles (Chapter 8), halogenation (Chapter 9), regiochemistry (Chapter 10), cluster modification (Chapter 11), heterofullerenes (Chapter 12), and higher fullerenes (Chapter 13). Methods described herein can be used to synthesize fullerene derivatives and adducts.

In particular, the active layer can comprise at least one n-type material, wherein the n-type material comprises at least one derivatized fullerene or fullerene derivative. The derivative compound can be, for example, an adduct. The terms "derivatized fullerene," "fullerene derivative" as used herein, can be used interchangeably and can be, for example, fullerenes comprising, from 1 to 84, or 1 to 70, or 1 to 60, from 1 to 20, from 1 to 18, from one to ten, or from one to six, or from one to five, or from one to three substituents each covalently bonded to, for example, one or two carbons in the spheroidal carbon compounds. The derivatized fullerene can comprise a fullerene covalently bonded by [4+2] cycloaddition to at least one derivative moiety, R.

An example of an n-type material is PCBM.

Examples of n-type materials are described in, for example, International Patent Publication No. WO/2008/018931 published on Feb. 14, 2008 and US Patent Publication 2008/0319207 published Dec. 25, 2008, both to Laird, et al. See also, for example, for n-type small molecules and/or polymers for use in OPVs: a) Shin, et al. *Chem. Mater.* 2007, 19, 1892-1894; b) Hoppe, et al. *Adv Polym Sci.* 2008, 214, 1; c) Panagiotis, et al. *Adv. Funct. Mater.* 2008, 18, 1; d) Frechet, J. M. J. et al. *Chem. Mater.* 2009, 21, 1775.

Solvent

The solvents can be halogenated or non-halogenated. The solvents useful for the presently claimed inventions can include, for example, halogenated benzenes, alkyl benzenes, halogenated methane, and thiophenes derivatives, and the like. More specifically, solvent can be for example chlorobenzene, dichlorobenzene, trichlorobenzene, xylenes, toluene, chloroform, 3-methylthiophene, 3-propylthiphene, 3-hexylthiophene, and mixtures thereof. At least two solvents can be used.

The solvent system can include at least two solvents, at least one first solvent and at least one second solvent (e.g., a solvent additive), which are different from each other. They can be organic solvents. Particularly useful solvent systems can be used as described in co-pending US patent application entitled "Solvent System for Conjugated Polymers," published as 2008/0299293, to Sheina et al., and co-pending US patent application entitled "Improved Solvent System," Ser. No. 12/541,500 filed Aug. 14, 2009, which are hereby incorporated by reference in their entirety.

Solvent Additives

Solvent additives can be used, wherein a relatively small addition of a component (e.g., 1-6 wt % or 1-3 wt %) can have a large impact on performance. For example, a primary or first solvent can be used in conjunction with a solvent additive. Solvent additives can be volatile and can be removed upon solvent removal. Or solvent additives can be less volatile and stay in the film upon solvent removal.

Different examples exist for solvent additives. For example, a solvent additive can comprise at least one heterocyclic ring. The heterocyclic ring can be, for example, at least one thiophene ring. The second solvent can be for example an alkylthiophene. In some instances the heterocyclic ring is not a nitrogen-containing ring. Or it can be a nitrogen containing ring. Thus, in some embodiments the second solvent is or is not a pyridine, pyrazine, pyrimidine, or a pyrrolidinone. In some embodiments, the heterocyclic ring includes at least one S atom and at least one O atom. Examples of suitable solvent additives include, but are not limited to, thiophene derivatives (i.e., substituted thiophenes). The benzene and/or thiophene ring may be substituted or unsubstituted in different positions on the ring. However, in some instances the thiophene derivatives do not contain halogen atoms. Alkylthiophenes and combinations thereof may be used as the second solvent. The alkyl group can be, for example, C1, C2, C3, C4, and the like up to and including C8, C12, C16, and C20. The alkyl group can be linear or branched. Specific examples of suitable alkylthiophenes include methylthiophene, ethylthiophene, propylthiophene, butylthiophene, pentylthiophene, hexylthiophene, heptylthiophene, octylthiophene, nonylthiophene, and decylthiophene. Fluorinated solvents and additives can be used.

Other examples of solvent systems can be used as described in the aforementioned co-pending US patent applications, in US Patent Publication entitled "Processing Additives for Fabricating Organic Photovoltaic Cells"2009/0108255 to Bazan et al., published on Apr. 30, 2009 or in Peet, et al., "Efficiency enhancement in low-bandgap polymer solar cells by processing with alkane dithiols," *Nat. Mater.*, 2007, 6, 497-500.

Device Preparation

Devices can be made comprising one or more layers comprising the polymers described herein and one or more electrodes, including anode and cathode. Layers can be built up on a substrate. See, for example, Chen et al., *Advanced Materials*, 2009, 21, 1-16.

Devices using the presently claimed inventions can be made using for example ITO as an anode material on a substrate. Other anode materials can include, for example, metals, such as Au, carbon nanotubes, single or multiwalled, and other transparent conducting oxides. The resistivity of the anode can be maintained below, for example, 15 Ω/sq or less, 25 or less, 50 or less, or 100 or less, or 200 or less, or 250 or less. The substrate can be rigid or flexible and can be, for example, glass, plastics (PTFE, polysiloxanes, thermoplastics, PET, PEN and the like), metals (Al, Au, Ag), metal foils, metal oxides, (TiOx, ZnOx, NiOx, and the like) and semiconductors, such as Si. The ITO on the substrate can be cleaned using techniques known in the art prior to device layer deposition.

A variety of layers can be included between the anode and the active layer of a solar cell or the emissive layer of an OLED. These layers are generally referred to as hole transport layer (HTL), hole injection layers (HIL), hole collection (HCL), electron blocking layers (EBL) and/or interlayers.

Various kinds of hole transport layers, hole injection layers, hole collection layers, and/or hole extraction layers can be used. For example, hole transport layers of various kinds are described in the following references: 1) U.S. Pat. No. 7,569,159, issued Aug. 4, 2009 to Hammond et al.; U.S. Ser. No. 11/826,394, filed Jul. 13, 2007, published Oct. 9, 2008 as 2008/0248313; U.S. Ser. No. 12/422,159, filed Apr. 9, 2009; U.S. Ser. No. 61/108,851, filed Oct. 27, 2008; and U.S. Ser. No. 61/115,877, filed Nov. 18, 2008.

Hole transport layers (HTL) can be added using, for example, spin casting, ink jetting, doctor blading, spray casting, dip coating, vapor depositing, or any other known deposition method.

The HTLs can be formed as films from, for example, PEDOT, PEDOT/PSS or TBD, or NPB, or PLEXCORE® OC inks (Plextronics, Pittsburgh, Pa.).

The thickness of the HTL or HIL layer can be, for example, from about a monolayer to about 10 nm or to about 300 nm thick, or from 30 nm to 60 nm, 60 nm to 100 nm, or 100 nm to 200 nm. The film then can be optionally dried and/or solvent and/or temperature treated and/or annealed at 110 to 200° C. for 1 min to an hour, optionally in an inert atmosphere.

Active layer thickness can be, for example, about 50 nm to about 250 nm, including for an OPV device.

The active layer can be formulated from a mixture of n-type and p-type materials. The n- and p-type materials can be mixed in a ratio of, for example, from about 0.1 to 4.0 (p-type) to about 1 (n-type) based on a weight, or from about 1.1 to about 3.0 (p-type) to about 1 (n-type) or from about 1.1 to about 1.5 (p-type) to about 1 (n-type). The amount of each type of material or the ratio between the two types of components can be varied for the particular application.

The active layer can be then deposited by spin casting, ink jetting, doctor blading, spray casting, dip coating, vapor depositing, or any other known deposition method, on top of the HTL or HIL film. The film is then optionally thermally annealed at, for example, about 40 to about 250° C., or from about 150 to 180° C., for about 10 min to an hour in an inert atmosphere. Solvent annealing can be also carried out as needed. Solvent annealing can be carried out at, for example, ambient temperature (for low boiling solvents). The film can be also optionally dried in solvent saturated and/or inert and/or vacuum atmosphere. The active layer can be also annealed with use of an electric field ("electric field annealing"). For example, a device can be cycled in an electric field which can in some instances improve performance. Internal heating may also contribute to electric field annealing.

A cathode layer can be added to the device, generally using, for example, thermal evaporation of one or more metals. Also, solution processing can be used. For example, a 1 to 15 nm Ca layer is thermally evaporated onto the active layer through a shadow mask, followed by deposition of a 10 to 300 nm Al layer.

A variety of layers can be included between the cathode and the active layer of a solar cell or the emissive layer of an OLED. These layers are generally referred to as electron transport layers (ETL), electron injection layers (EIL), hole blocking layers (HBL) and/or interlayers.

In some embodiments, an optional interlayer may be included between the active layer and the cathode, and/or between the HTL or HIL and the active layer. This interlayer can be, for example, from 0.5 nm to about 100 nm, or from about 1 to 3 nm, thick. The interlayer can comprise an electron conditioning, a hole blocking, or an extraction material, such as LiF, BCP, metal oxides, bathocuprine, fullerenes or fullerene derivatives, such as C60, C70, C84 and other fullerenes and fullerene derivatives discussed herein.

Electron transport layers can be used in, for example, solar cell devices. See, for example, U.S. patent application No. 61/116,963 filed Nov. 21, 2008.

Interfacial modification layers can be used as described in, for example, PCT/US2009/006236 filed Nov. 20, 2009 (Plextronics, Inc.). The interfacial modification layer can comprise, for example, an organic semiconductor which is doped by, for example, a metal (e.g., BPhen:Yb). The interfacial modification layer can be prepared by vacuum deposition methods. It can have a thickness of, for example, 3 nm to 25 nm, or 5 nm to 15 nm. An Al layer can be disposed on top.

The devices can be then encapsulated using a glass cover slip sealed with a curable glue, or in other epoxy or plastic coatings. Cavity glass with a getter/desiccant may also be used.

In addition, the active layer can comprise additional ingredients including, for example, surfactants, dispersants, oxygen and water scavengers.

The active layer can comprise multiple layers or be multi-layered.

The active layer composition can be formed from an ink comprising a mixture as a film.

Films and devices can be annealed before use and testing. Thermal/electrical annealing and solvent annealing can be carried out.

Inverted solar cells can be made. See, for example, Chen et al. *Advanced Materials*, 2009, 21, 1-16. Tandem solar cells can be made.

Device Testing

Known solar cell parameters can be measured including for example $J_{SC}$ (mA/cm$^2$) and Voc (V) and fill factor (FF) and power conversion efficiency (%, PCE) by methods known in the art. See for example Hoppe article cited above and references cited therein.

Oriel Solar Simulators can be used to determine PV properties including, for example, FF, Jsc, Voc, and efficiencies. The simulator can be calibrated by methods known in the art including, for example, calibration with a KG5-Si reference cell. External quantum efficiency (EQE) can be measured.

Other properties for the inks, films, and devices can be measured by methods known in the art.

Power conversion efficiency (PCE) can be, for example, at least about 1%, or at least about 2%, or at least about 3%, or at least about 4%, or at least about 5%, or at least about 6%, or at least about 7%, or at least about 8%, or higher.

Fill factor, which can be expressed as a number between 0 and 1, or a percentage between 0 and 100%, can be, for example, at least about 0.4 (40%), or at least about 0.5 (50%), or at least about 0.6, or at least about 0.7, or at least about 0.8, or at least about 0.9 or higher.

Open circuit voltage ($V_{oc}$) in V can be, for example, at least about 0.3, or at least about 0.4, or at least about 0.5, or at least about 0.6 V, or at least about 0.7 V, or at least about 0.8 V, or at least about 0.9 V, or at least about 1.0 V, or at least about 1.1 V, or at least about 1.2 V, or at least about 1.3 V, or higher.

Short circuit current ($J_{SC}$) can be, for example, at least about 0.5, or at least about 0.6, or at least about 0.7, or at least about 0.8, or at least about 0.9, or at least about 1.0, or at least about 2.0, or at least about 3.0, or at least about 4.0, or at least about 5.0, or at least about 10.0, or higher (mA/cm$^2$).

Energy Harvesting

In addition, devices and applications can be made and carried out in energy harvesting (EH). Energy harvesting is an indoor application of photovoltaic technology, whereby an EH device harnesses ambient light, typically fluorescent office lighting, for energy storage or direct use for a wide variety of low power applications. For example, a typical office environment can have light levels of about 1000 LUX, or about 0.5% (0.5 mW/cm^2) of the incident radiant energy of 1 sun. This represents the total amount of energy that can be harvested in these environments and high efficiency photovoltaic technology, suited to these light levels are important for leveraging novel applications and can be a replacement for coin-cell batteries (or equivalent). Typical outdoor solar technology, such as mc-Si c-Si, have low performance at indoor lighting levels due to a high amount of Voltage loss. Organic PV and a-Si are well suited to low light levels and OPV can be a more cost effective solution vs. a-Si and thus can be used in EH technology.

Polymers can be designed to exhibit a 'flat' response with decreasing light levels and represent a novel high-performance technology of indoor EH applications. Typical device stacks for EH applications are very similar to their outdoor solar analogs and a typical configuration is ITO/ZnO/conjugated polymer:PCBM[C60]/HTL/Ag.

Devices can be tested at 1000 LUX and one can determine the power density at this standard luminance level. In addition, one can measure devices at a variety of light intensities to understand how device parameters change with changes in ambient light level. One can also measure leakage current at reverse bias to help understand the diode quality as poor diode quality can result in lower performance at lower and lower light levels.

Photodetection

In addition, organic photodetection (OPD) is an application of PV technology where a circuit can be controlled by the presence or absence of radiant energy impinging on the said circuit, which contains a photosensitive device. The use of organic photodetectors offers an advantage of cost and integration that may not be possible with incumbent technology, namely a-Si.

OPD devices can be fabricated very similarly to a solar OPV device and a typical configuration is: ITO/HTL/conjugated polymer:Fullerene n-type/Cathode, where the cathode can be Ca/Al, or organic small molecule, doped with a metal, or organic material and capped with a metal such as Aluminum.

There are four quadrants of a current voltage plot which are defined by positive and negative current and voltage (I=+c/−v, II=+c/+v (OLED), III=−c/−v (OPD), IV=−c/+v (OPV)). OLED devices operate in quadrant II, OPVs in quadrant IV and OPDs in quadrant III.

For OPD the product of current and voltages are always positive thus this is a device which requires power input. The input power is provided to the OPD circuit and when the OPV cell is exposed to light, a massive gain (several decades, up to >10^4) in current can occur. This provides a 'gate' which allows the circuit to differentiate between light (on) and dark (off) states, thus allowing for photodetection.

For OPD technology, key parameters include 1) current density (expressed as mA/cm^2 and higher is better) at a negative voltage (at typically −1 or −2 V) and 2) the noise floor in the dark state, typically expressed as a current density (nA/cm^2) and the lower the better. Parameter #1 is proportional to the quantum efficiency of the device and devices which are most efficient at generating current with the input radiant energy are best. For #2, device design is necessary to reduce the leakage current (or noise floor) and the photoactive layer materials should have as low a carrier density in the off state as possible, ie not doped.

Materials described herein can offer high quantum efficiency, low doping due to deep HOMO, and air processibility that is amenable to rapid OPD device development.

PART III. WORKING EXAMPLES

Method 1:

Example 1

Synthesis of 2,5-bis(trimethylstannyl)thieno[3,2-b]thiophene

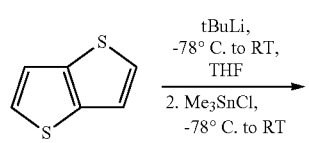

-continued

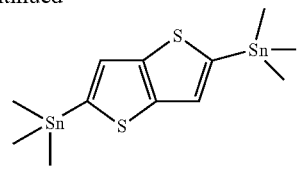

In a 3-neck round bottom flask equipped with an argon inlet and an addition funnel, thieno[3,2-b]thiophene (7.5 g, 54 mmol) was dissolved in tetrahydrofuran (1 L). After the solution was cooled to −78° C. using an isopropanol/dry ice bath, t-BuLi (100 mL, 170 mmol) was transferred by cannula to the addition funnel. The organolithium reagent was then added dropwise. After completion of the addition, the mixture was stirred for 20 min at −78° C. then warmed up with an isopropanol bath at room temperature for 30 minutes during which a yellow precipitate formed. The solution was cooled back at −78° C., and after cannula transfer to the addition funnel, trimethyltin chloride (200 mL of 1 M solution in THF, 200 mmol) was added dropwise. During addition of trimethyltin chloride, the precipitate disappeared and the solution turned light brown. After warming to room temperature the solution was stirred for 30 minutes then was poured into ice-cold water. The aqueous phase was further extracted with hexane. The combined organic phases were washed with cold water then dried with magnesium sulfate. After filtration, the solvent is evaporated under vacuum to yield a grey-brown solid. The product was purified by precipitation of a chloroform solution into methanol followed by filtration (13.2 g, 53%). Spectral data: $^1$H NMR (CDCl$_3$, 300 MHz): $\delta_H$ 0.41 (s, 18H), 7.26 (s, 2H). $^{13}$C (CDCl$_3$, 75 MHz): $\delta$ 7.99, 126.29, 141.4, 147.62.

Example 2

Synthesis of methyl 2-bromothiophene-3-carboxylate

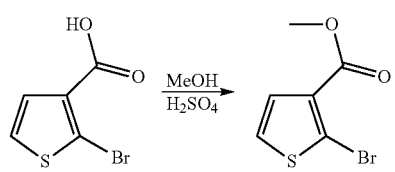

Thiophene-2-bromo-3-carboxylic acid (10 g, 45 mmol) was placed in a dry 3-neck round bottom flask equipped with an argon inlet and a water condenser. Dry methanol (100 mL) was added to the flask along with a catalytic amount of cc. sulfuric acid (1 mL). The reaction completion was determined by NMR analysis. When complete, the reaction was cooled to room temperature. The methanol was evaporated and the resulting product was purified via column chromatography, using a 100% hexane to 60% hexane/40% ethyl acetate gradient to yield a slightly yellow clear oil (9 g, 91%).

Spectral data: $^1$H NMR (CDCl$_3$, 300 MHz): $\delta_H$ 3.89 (s, 3H), 7.23 (d, 5.76), 7.36 (d, 5.78 Hz).

$^{13}$C NMR (CDCl$_3$, 75 MHz): $\delta$ 52.13, 120.15, 126.09, 129.48, 131.07, 162.61.

Example 3

Synthesis of dimethyl 2,2'-(thieno[3,2-b]thiophene-2,5-diyl)bis(thiophene-3-carboxylate)

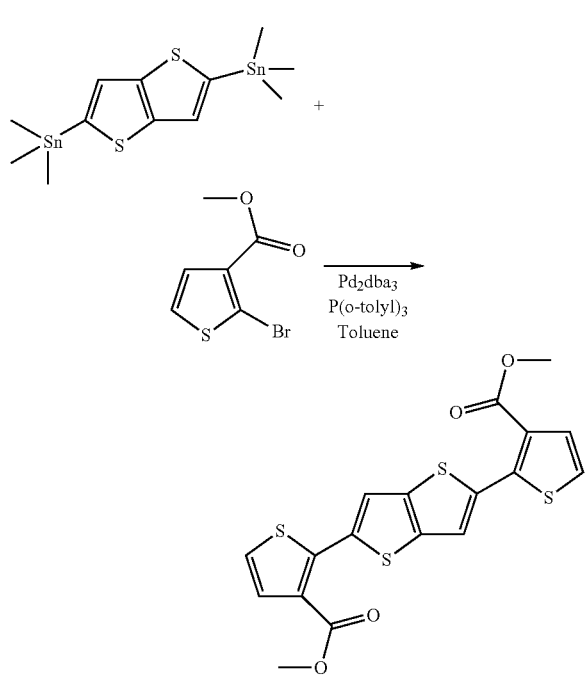

In a glove box, 2,5-bis(trimethylstannyl)thieno[3,2-b]thiophene (2.67 g, 5.7 mmol), methyl 2-bromothiophene-3-carboxylate (2.5 g, 11.31 mmol), Pd$_2$dba$_3$ (131 mg, 0.14 mmol) and P(o-tolyl)$_3$ (174 mg, 0.57 mmol) were charged in a Schlenk flask. The flask was connected to an argon/vacuum line and its side arm was purged 5 times before the flask was open to argon. Toluene (100 mL, purged overnight with argon) was added and the mixture was purged five times with vacuum argon cycles. The flask was placed in a preheated bath at 110° C. and the mixture was stirred overnight. Over time a yellow-green precipitate formed. After cooling, the precipitate was filtered and washed with hexane. NMR analysis indicated product was pure (2 g, 42%) and as a result it was used without further purification.

Spectral data: $^1$H NMR (CDCl$_3$, 300 MHz): $\delta_H$ 3.85 (s, 6H), 7.25 (d, 2H, 5.46 Hz), 7.51 (d, 2H, 5.39 Hz).

$^{13}$C (CDCl$_3$, 75 MHz): $\delta$ 52.11, 121.47, 124.77, 128.07, 130.88, 147.69, 163.69.

Example 4

Synthesis of (2,2'-(thieno[3,2-b]thiophene-2,5-diyl)bis(thiophene-3,2-diyl))bis(bis(4-(2-ethylhexyl)phenyl)methanol)

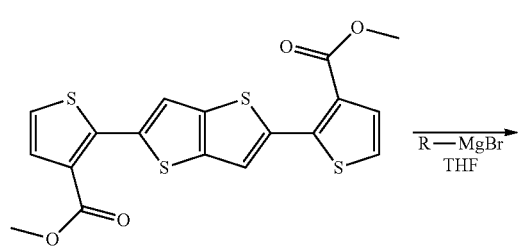

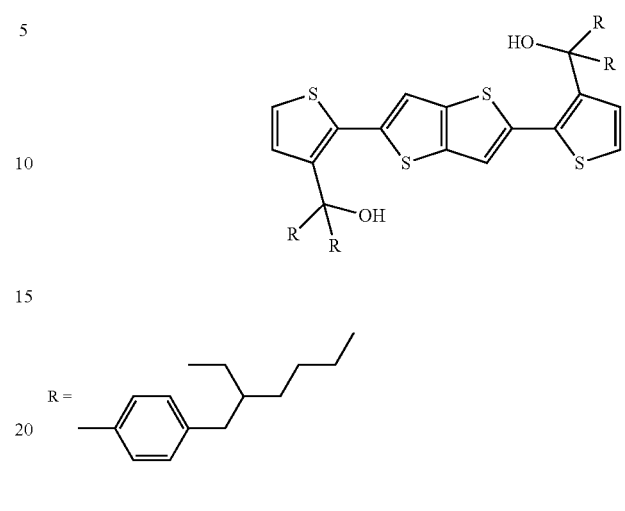

A flame-dried 3-neck round bottom flask equipped with an argon inlet, a water condenser and an addition funnel, was charged with magnesium (0.81 g, 33 mmol) and anhydrous THF (30 mL) that was added via deoxygenated syringe. A few crystals of iodine were added to initiate reaction, and 4-(2-ethylhexyl)-phenylbromide (7.5 g, 27.9 mmol) was added dropwise. The solution was refluxed for a few hours, until GC analysis of an aliquot showed no starting material remained. After cooling, dimethyl 2,2'-(thieno[3,2-b]thiophene-2,5-diyl)bis(thiophene-3-carboxylate) (2.0 g, 4.8 mmol) was added in one portion. And the solution was refluxed and its progress was monitored by TLC. Upon reaction completion, the reaction was cooled and poured in 1M HCl solution. The aqueous phase was extracted with MTBE. The combined organic phases were washed with water then dried with anhydrous magnesium sulfate. After filtration the solvent was removed under vacuum, and the final product, a dark orange viscous oil, was obtained after silica column chromatography using 100% hexane to 100% CHCl$_3$ gradient (2.6 g, 48%).

Example 5

Synthesis of 5,5,10,10-tetrakis(4-(2-ethylhexyl)phenyl)-3,5,8,10-tetrahydro-cyclopenta[1,2-b:5,4-b']dithiophene[2',1':4,5]thieno[2,3-d]thiophene

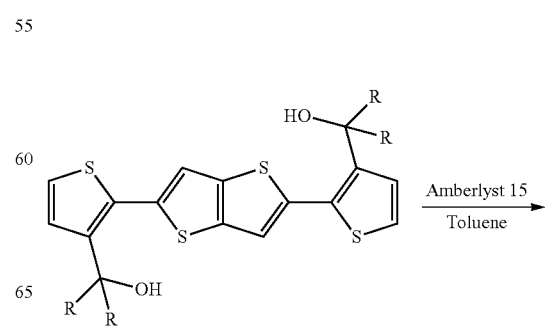

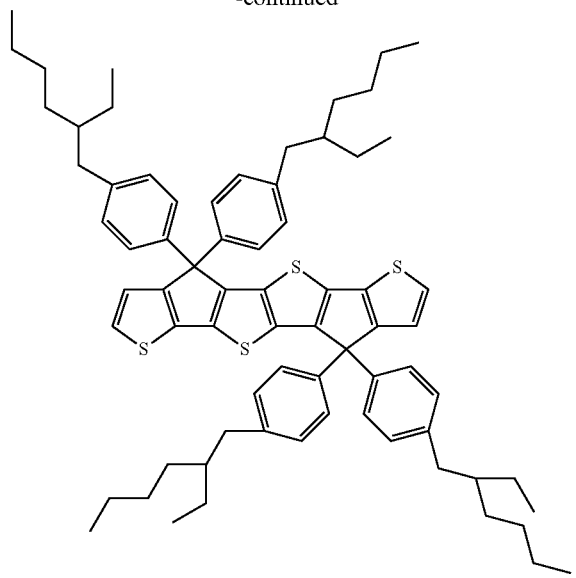

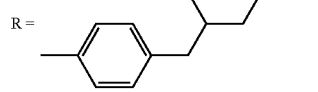

(2,2'-(Thieno[3,2-b]thiophene-2,5-diyl)bis(thiophene-3,2-diyl))bis(bis(4-(2-ethylhexyl)phenyl)methanol) (2.1 g, 1.78 mmol) was charged in a schlenk flask under argon atmosphere. Toluene (200 mL, bubbled overnight with argon) was added along with Amberlyst 15 (1 g). The flask was purged with vacuum-argon cycles 5 times then placed in a preheated bath at 110° C. The reaction was monitored by TLC using hexane as eluent. When the reaction was completed, it was cooled to room temperature, and immediately filtered through silica plug to yield the product as a yellow-orange solid (1.1 g, 57%). Spectral data: $^1$H NMR (CDCl$_3$, 300 MHz): $\delta_H$ 0.72-0.96 (t, 24H, 7.39 Hz) 1.12-1.35 (m, 32H), 1.43-1.6 (m, 4H), 2.46 (d, 8H, 6.9 Hz), 7.03 (d, 8H, 8.21 Hz), 7.07 (d, 2H, 4.86 Hz), 7.13 (d, 8H, 7.95 Hz), 7.15 (d, 2H, ~3.9 Hz). $^{13}$C (CDCl$_3$, 75 MHz): $\delta$ 10.94, 14.34, 23.2, 25.62, 29.01, 32.49, 39.9, 41.01, 62.11, 123.54, 125.36, 127.83, 129.48, 135.15, 137.31, 140.82, 148.68, 157.24.

Example 6

Synthesis of (5,5,10,10-tetrakis(4-(2-ethylhexyl)phenyl)-3,5,8,10-tetrahydro-cyclopenta[1,2-b:5,4-b']dithiophene[2',1';4,5]thieno[2,3-d]thiophene-2,7-diyl)bis(trimethylstannane)

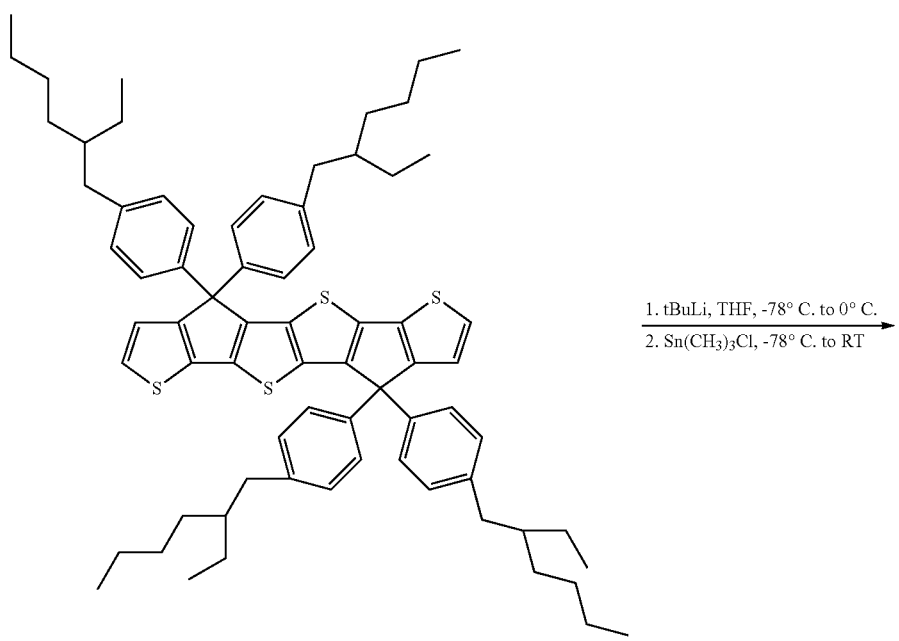

-continued

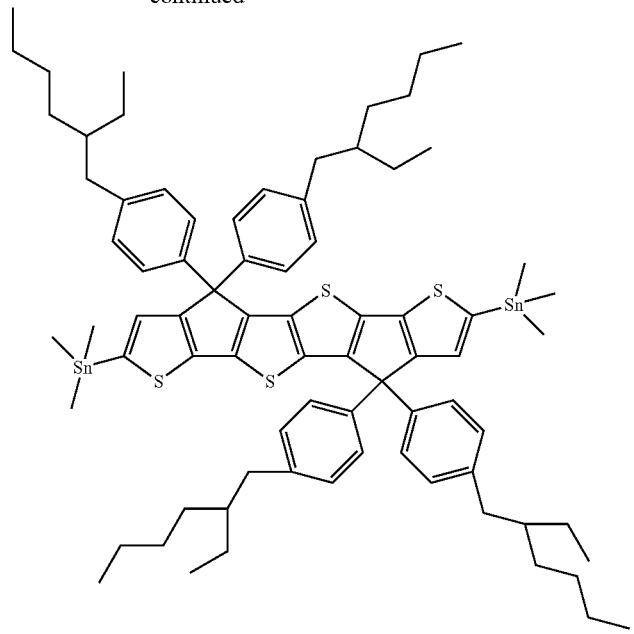

The starting compound (530 mg, 0.49 mmol) was dissolved in THF (150 mL) in a dry schlenk flask. The solution was cooled to −78° C. and ter-butyllithium (0.87 mL of 1.7 M solution, 1.5 mmol) was added dropwise via syringe. After completion of the addition, the mixture was stirred 60 min at −78° C. the 15 minutes at room temperature (using IPA bath at RT) during which the solution turned from orange to dark brown-orange. The solution was cooled back at −78° C., and trimethyltin chloride (2 mL of 1M solution in THF, 2 mmol) was added dropwise. The mixture is warmed to room temperature following completion of the addition and stirred at that temperature for 30 minutes then was poured into ice-cold water. The aqueous phase was further extracted with hexane. The combined organic phase were combined and washed with cold water then dried with magnesium sulfate. After filtration, the solvent was evaporated under vacuum to yield an orange solid. The product was purified by precipitation of a chloroform solution into methanol followed by filtration (540 mg, 78%).

Spectral data: $^1$H NMR (CDCl$_3$, 300 MHZ) $\delta_H$ 0.36 (s, 18H), 0.83 (t, 12H, 6.04 Hz), 0.84 (t, 12H, 7.21 Hz), 1.13-1.34 (m, 32H), 1.46-1.59 (m, 4H), 2.46 (d, 8H, 6.86 Hz), 7.03 (d, 8H, 8.18 Hz), 7.07 (s, 2H), 7.13 (d, 8H, 8.36 Hz).

Example 7

Synthesis of Donor-Acceptor random copolymer based on 5,5,10,10-tetrakis(4-(2-ethylhexyl)phenyl)-3,5,8,10-tetrahydro-cyclopenta[1,2-b:5,4-b']dithiophene[2',1':4,5]thieno[2,3-d]thiophene

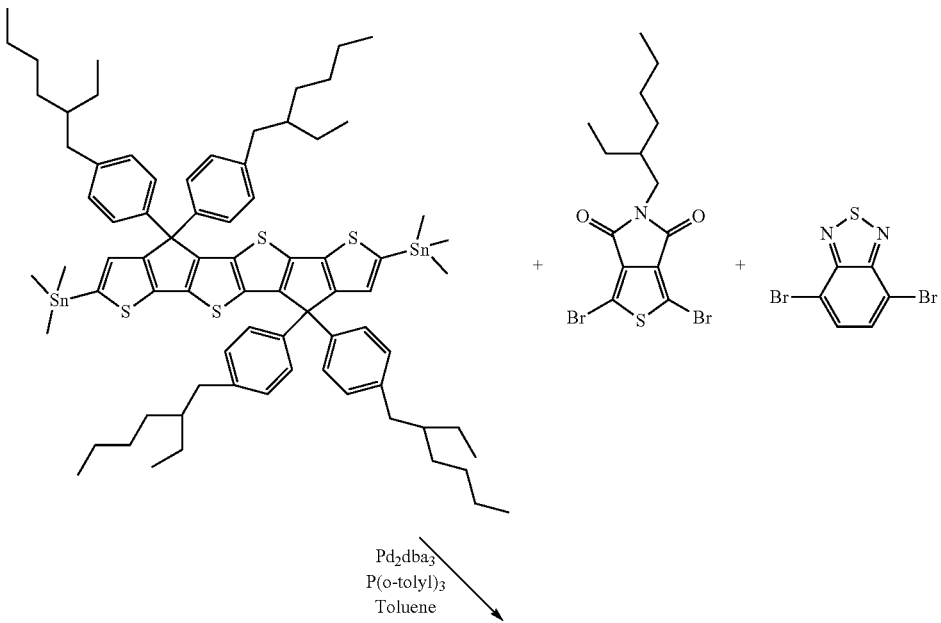

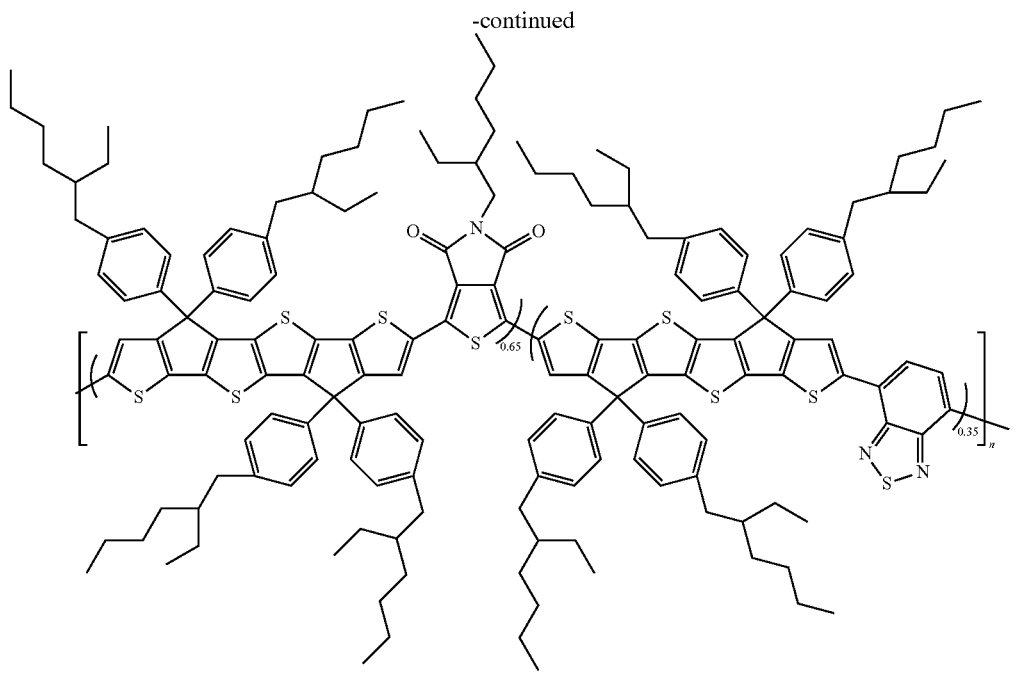

In a glove box, 1,3-dibromo-5-(2-ethylhexyl)-4H-thieno[3,4-c]pyrrole-4,6(5H)-dione (43.78 mg, 0.10 mmol), (5,5,10,10-tetrakis(4-(2-ethylhexyl)phenyl)-3,5,8,10-tetrahydro-cyclopenta[1,2-b:5,4-b']dithiophene[2',1':4,5]thieno[2,3-d]thiophene-2,7-diyl)bis(trimethylstannane) (224 mg, 0.159 mmol), 4,7-dibromobenzo[c][1,2,5]thiadiazole (16.38 mg, 0.056 mmol), Pd$_2$dba$_3$ (3.64 mg, 0.004 mmol), P(o-tolyl)$_3$ (4.84. mg, 0.016 mmol) were charged in a 100 ml Schlenk flask. After connecting the flask to vac/argon line, the side arm was flushed with 5 vacuum-argon cycles and the flask was opened to argon. Toluene (10 mL), degassed with argon overnight, was added. The flask was purged five times through vacuum-argon cycles then placed in a preheated flask at 110° C. for 48 hours. After cooling, methanol was added to precipitate the polymer. The polymer was filtered through Soxhlet thimble and Soxhlet extraction was performed with methanol, MTBE, hexane and chloroform (100 mg). Molecular weight was determined by GPC in chlorobenzene (1 mL/min at 80° C.) vs. polystyrene standards: M$_n$=28,100, M$_w$=47,800, PDI=1.7.

In a solar cell device, the V$_{oc}$ for this material was 0.72 V. See Table I. HOMO level (AC2, eV) was 5.15. In contrast, HOMO level for BPP-1 was 5.31 eV.

Example 8

Synthesis of Donor-Acceptor random copolymer based on 5,5,10,10-tetrakis(4-(2-ethylhexyl)phenyl)-3,5,8,10-tetrahydro-cyclopenta[1,2-b:5,4-b]dithiophene[2',1':4,5]thieno[2,3-d]thiophene and 5,5'-bis(2-ethylhexyl)-4H,4'H-[1,1'-bithieno[3,4-c]pyrrole]-4,4',6,6'(5H,5'H)-tetraone -continued

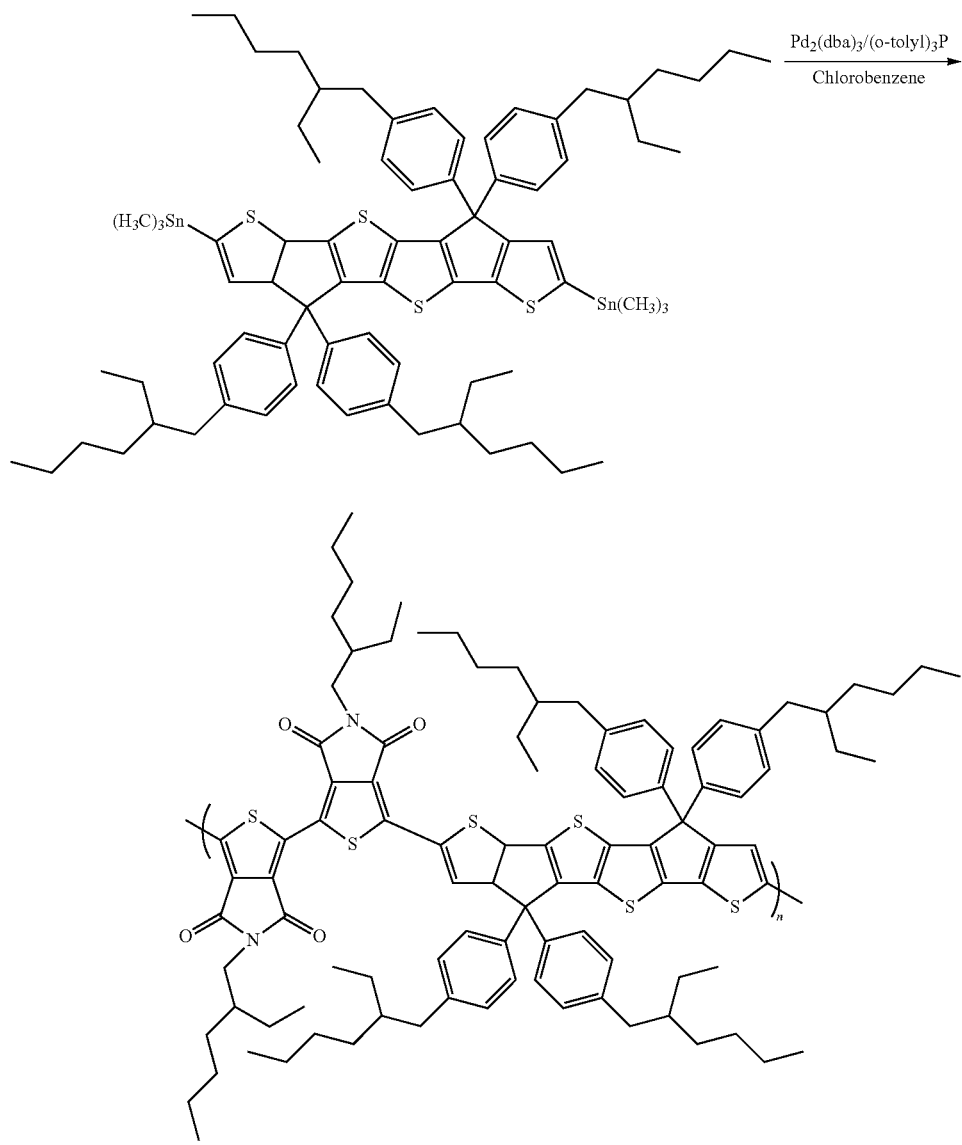

In a glove box, (5,5,10,10-tetrakis(4-(2-ethylhexyl)phenyl)-3,5,8,10-tetrahydro-cyclopenta[1,2-b:5,4-b'] dithiophene[2',1':4,5]thieno[2,3-d]thiophene-2,7-diyl)bis (trimethylstannane) (0.40 mmol), 1-bromo-3-[3-bromo-5-(2-ethylhexyl)-4,6-dioxo-thieno[3,4-d]pyrrol-1-yl]-5-(2-ethylhexyl)thieno[3,4-c]pyrrole-4,6-dione (0.40 mmol), tris (dibenzylideneacetone)dipalladium(0) (9.2 mg, 0.010 mmol) and tris(o-tolyl)phosphine (12 mg, 0.040 mmol) were charged into a flame dried 50 mL Schlenk flask. The reaction flask was removed from the glove box and 10 mL of deoxygenated chlorobenzene were added via syringe. The mixture was evacuated and refilled with argon five times. The reaction flask was immersed into a 110° C. oil bath and left stirring under an argon stream for 2 days. After cooling to room temperature, 40 mL of methanol were added to the reaction mixture. The polymer was collected via filtration and purified by consecutive Soxhlet extractions in sequence with methanol, MTBE, hexane, and chloroform. The chloroform solution was passed through celite to remove catalyst residuals, and solvent was removed under vacuum to yield polymer. The polymer was re-dissolved in a small amount of chloroform, re-precipitated in the mixture of IPA, water and methanol, isolated via centrifuge and dried (200 mg). Molecular weight was determined by GPC in chlorobenzene (1 mL/min at 80° C.) vs. polystyrene standards: $M_n$=31,500, $M_w$=91,350, PDI=2.9. The polymer was called BPP-1, and solar cell preparation and testing performance is shown in Table I.

Example 9

Device Testing

Inks and devices were prepared according Table I, and the devices were tested and the results are shown in Table I.

TABLE I

Photovoltaic Performance of single layer OPVs based on Donor-Acceptor polymers comprising dioxypyrrolo-functionality

| Polymer Exp. # | n-type | p/n ratio | Conc/Solvent/additive[1] | HIL | Cathode | Anneal T° C./t/atm[2] | $J_{SC}$ mA/cm² | $V_{OC}$ (V) | FF | η(%) |
|---|---|---|---|---|---|---|---|---|---|---|
| APP-1 | C70PCBM | 1:2 | 0.011/CHCl₃:oDCB (66:34) | HIL A | Ca/Al | NA | 6.41 | 1.05 | 0.50 | 3.49 |
| | C70PCBM | 1:2 | 0.011/CHCl₃:oDCB (66:34) | HIL A | Ca/Al | NA | 6.45 | 1.05 | 0.50 | 3.56 |
| (Ex. 8) BPP-I | C70PCBM | 1:2 | 0.0157/CB:TCB:DBT (90:10 + 3) | HIL A | Ca/Al | NA | 7.06 | 0.87 | 0.45 | 2.83 |
| | C70PCBM | 1:2 | 0.0157/CB:TCB:DBT (90:10 + 3) | HIL A | Ca/Al | NA | 6.45 | 0.87 | 0.45 | 2.78 |
| Ex 7 | C70PCBM | 1:2 | 0.0157/TCB:ODCB (80:20) | HIL A | Ca/Al | NA | 4.01 | 0.72 | 0.45 | 1.3 |

DBT—dibromotoluene

[1] oDCB:DIO—dichlorobenzene:diiodooctane (97:3%); TCB—trichlorobenzene

[2] GB—glove box (N₂); Sol—solvent atmosphere (CHCl₃) for 15 minutes

Note: HIL A is an HIL ink formulation comprising 96.860 parts water; 2.826 parts Nafion (sulfonated perfluorinated copolymer); and 0.314 parts sulfonated polythiophene as described in PCT publication WO 2008/073149.

Comparative Example A

U.S. Ser. No. 12/828,121 filed Jun. 30, 2010 and Ser. No. 12/874,163 filed Sep. 1, 2010 describe synthesis and structures relevant to APP-1. Polymerization methods are described herein.

Example

Synthesis of poly(3-(5,6-bis(2-ethylhexyl)naphtho[2,1-b:3,4-b']dithiophen-2-yl)-alt-5,5'-bis(2-ethylhexyl)-4H,4'H-[1,1'-bithieno[3,4-c]pyrrole]-4,4',6,6'(5H,5'H)-tetraone)

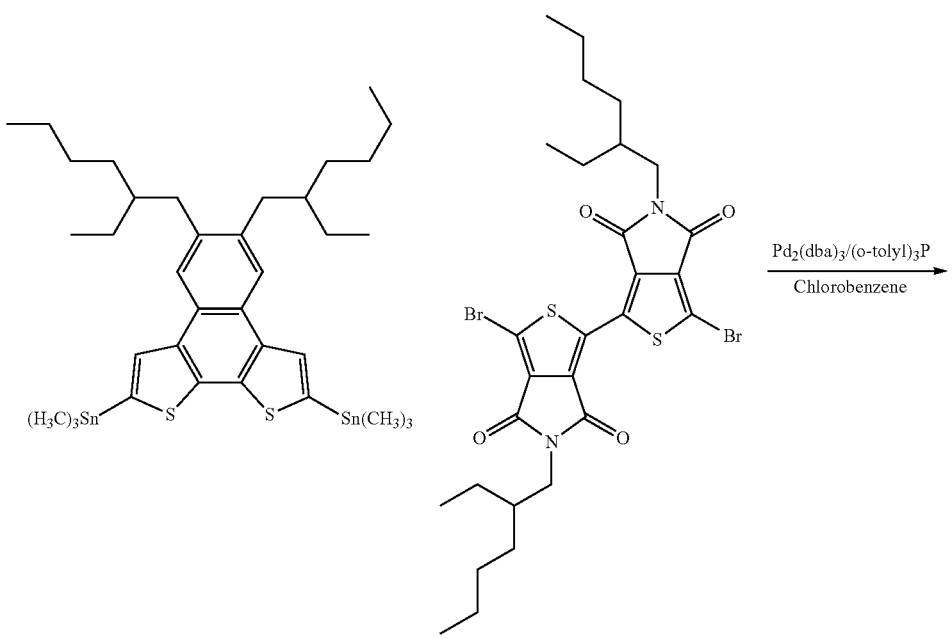

-continued

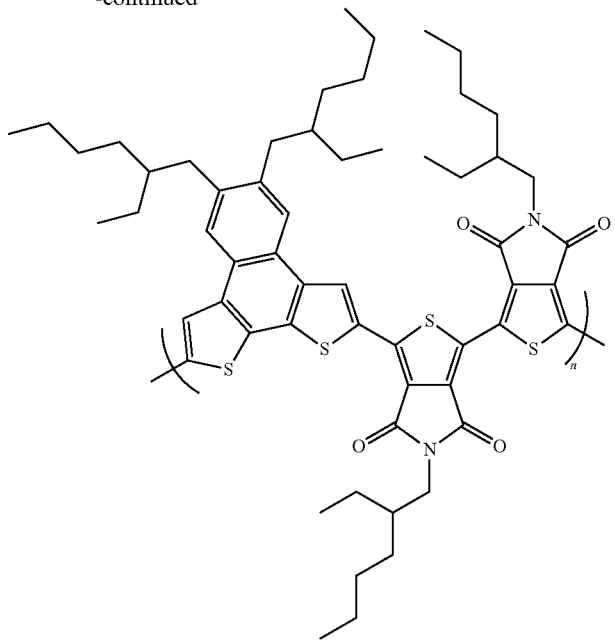

In a glove box, 3,3'-dibromo-5,5-bis(2-ethylhexyl)-4H,4'H-[1,1'-bithieno[3,4-c]pyrrole]-4,4',6,6'(5H,5'H)-tetraone (304 mg, 0.44 mmol), (5,6-bis(2-ethylhexyl)naphtho[2,1-b:3,4-b']dithiophene-2,9-diyl)bis(trimethylstannane) (350 mg, 0.44 mmol), Pd$_2$dba$_3$ (10 mg, 0.011 mmol), P(o-tolyl)$_3$ (13 mg, 0.044 mmol) were charged in a 100 mL schlenk flask. The flask was removed from a glove box, connected to a vac/argon line, and the side arm was flushed with five vacuum-argon cycles, after which the flask was open to argon. Anhydrous toluene (20 mL), degassed with argon overnight, was added via a deoxygenated syringe. The flask was purged five times with argon, and immersed into a preheated to 110° C. flask for 48 hours. After cooling, methanol was added to precipitate the polymer. The polymer was filtered through Soxhlet thimble and Soxhlet extraction was performed in sequence with methanol, MTBE, hexane and chloroform. The final polymer was isolated as a chloroform insoluble fraction (270 mg, 65%). Molecular weight was determined by GPC in chlorobenzene (1 mL/min at 80° C.) vs. polystyrene standards: $M_n$=23,700, $M_w$=168,300, PDI=7.1. The polymer was labeled APP-1, and solar cell preparation and testing performance is shown in Table I.

Example 10

Testing of Polymer Properties

FIG. 1 (EQE data) compares the polymer of Example 8 with a competitive polymer APP-1 which does not comprise structure (I).

Both polymers display absorption and EQE with very sharp onset. However, in the case of the Example 8 polymer, the absorption is pushed all the way to 780 nm, from about 700 nm compared to APP-1. The band edge is almost 0.2 eV bathochromically shifted and at an optimal location for maximum light absorption.

Figure 2:
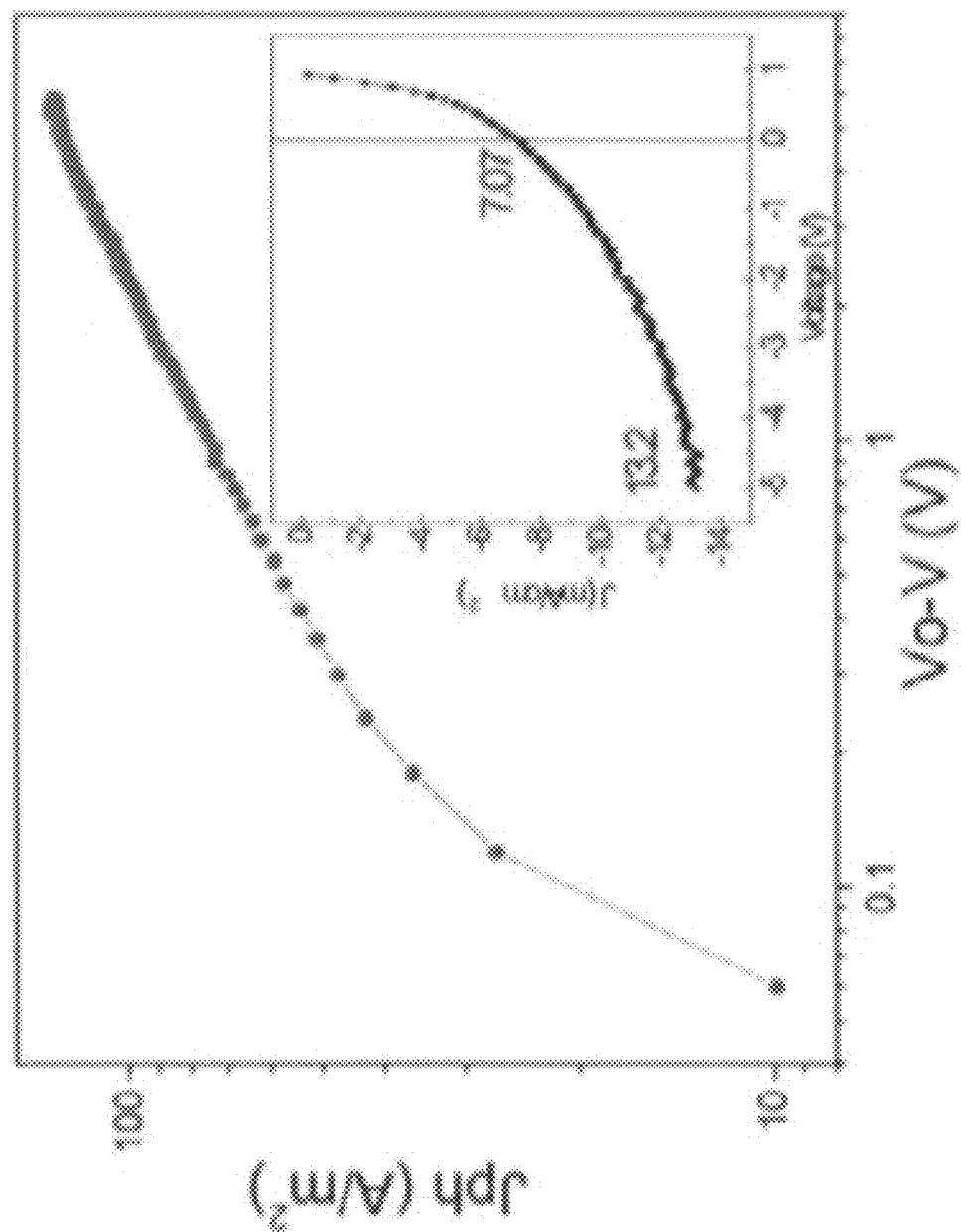
FIG. 2 illustrates reverse bias data for several polymers.

Both materials showed high efficiency (3.56% for APP-I and 2.83% for Example 8, see Table I). However, reverse bias measurement indicated a much higher reverse bias current for Example 8 compared to APP-1, reflective of its optimized absorption. See FIG. 2.

Additional EQE data are provided in FIG. 3. PV2000 materials are available from Plextronics, Inc. (Pittsburgh, Pa.).

Synthesis Method 2:

Example 11-A

Synthesis of tetrabromothienothiophene

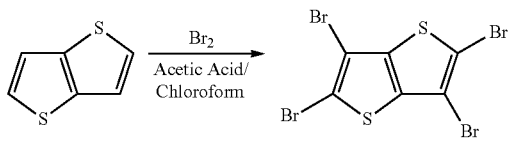

In a 3 neck round bottom flask equipped with an addition funnel, a water condenser and a nitrogen inlet, thieno[3,2-b] thiophene was dissolved in a mixture of acetic acid and chloroform. For safety, the top of the water condenser was vented into an Erlenmeyer containing a 5M NaOH solution so as to quench HBr gas. Bromine was added carefully. After 1 hour stirring, more bromine was added to the reaction and the mixture was stirred for another hour. An aliquot was tested by gas chromatography, indicating the reaction was not complete. As a result, more bromine was added. The reaction was then refluxed overnight, and a large amount of solids precipitated. A sample analyzed by gas chromatography indicated reaction completion. The mixture was then allowed to cool back to room temperature. The precipitate was filtered, washed with water and methanol. The solids were then dried under vacuum. GC-MS showed a single peak, [M+]=455.0.

Example 11-B

Synthesis of 3,3'-dibromothienothiophene

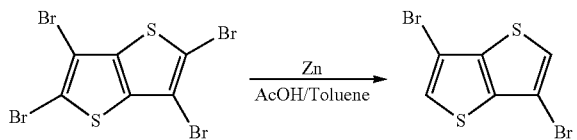

In a 3-neck flask equipped with a water condenser, tetrabromothienothiophene (20 g, 44 mmol), zinc powder (5.74 g, 88 mmol) were added to a mixture of acetic acid (500 mL) and toluene (200 mL). A few drops of 1M hydrochloric acid were also added for activation of zinc surface. The mixture was refluxed until gas chromatography indicated a complete reaction. After cooling to room temperature, the solution was concentrated down and the resulting precipitate was filtered through Buchner funnel.

Example 12

Synthesis of thieno[3,2-b]thiophene-3,6-diylbis(thiophen-3-ylmethanol)

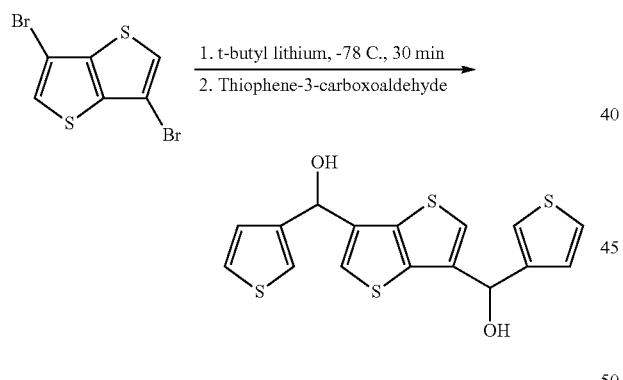

In a flame-dried schlenk flask under argon atmosphere, 3,3'-dibromothienothiophene was dissolved in diethylether. The solution was cooled down to −90° C. (MeOH+liq. N2 bath), and n-butyllithium was added dropwise. After 30 minutes stirring at −90° C., a solution of thiophene-3-carboxaldehyde in diethyl ether was added dropwise at −80° C. The mixture was then allowed to slowly warm up back to room temperature. A solution of 1M HCl was added to quench any reactive lithiated species. The aqueous phase was extracted with MTBE three times. The combined organic layers were washed with water three times, then dried with magnesium sulfate. After evaporation, the resulting solid was purified by column chromatography (100% $CHCl_3$ to 20% EtOAc/$CHCl_3$).

Example 13

Prophetic Example: Synthesis of thieno[3,2-b]thiophene-3,6-diylbis(thiophen-3-ylmethanone)

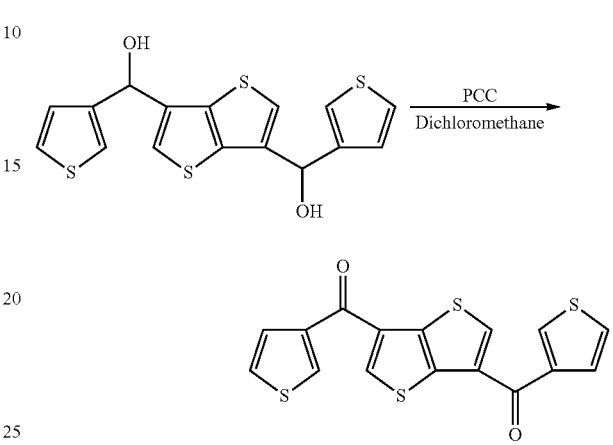

To a solution of thieno[3,2-b]thiophene-3,6-diylbis(thiophen-3-ylmethanol) in dichloromethane at 0° C. was added pyridinium chlorochromate. The mixture was allowed to warm up at room temperature and stirred for 4 hours. The mixture was then filtered through celite. The solvent was evaporated and the resulting product was purified by column chromatography.

Example 14

Synthesis of 3,6-bis(thiophen-3-ylmethyl)thieno[3,2-b]thiophene

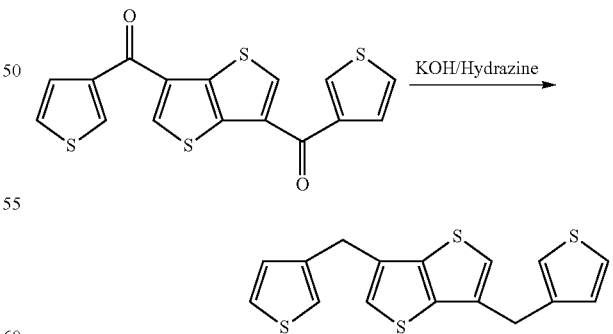

This conversion can be accomplished using the Huang-Minlon modification of the Wolff-Kishner reaction, as described in Vogel's textbook of *Organic Chemistry* (5th Edition) page 820.

Prophetic Example 15

Synthesis of 3,6-bis(9-(thiophen-3-yl)heptadecan-9-yl)thieno[3,2-b]thiophene

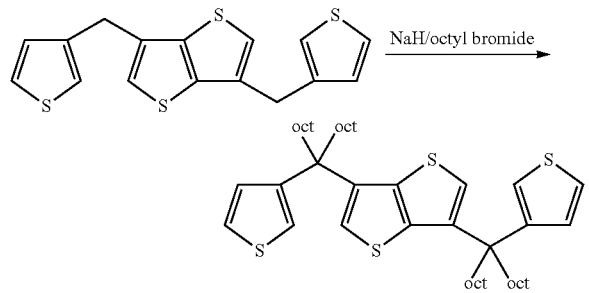

To a suspension of sodium hydride in THF is added a THF solution of 3,6-bis(thiophen-3-ylmethyl)thieno[3,2-b]thiophene. Octyl bromide is then added and the mixture is refluxed until reaction completion, as determined by TLC. The reaction is then poured into cold water, extracted with MTBE and combined organic phases are washed with water. After drying the organic phase with magnesium sulfate and filtering through Buchner the solvent is evaporated. The resulting product can be purified by column chromatography.

Prophetic Example 16

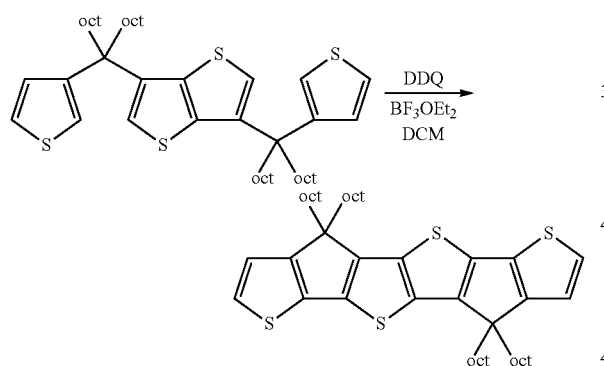

A dry 500 mL 3-neck flask, flushed with dry nitrogen, is charged with of 3,6-bis(9-(thiophen-3-yl)heptadecan-9-yl)thieno[3,2-b]thiophene (1 eq.). The flask is evacuated and backfilled with nitrogen 3 times. Dry $CH_2Cl_2$ is added to the flask via cannula. The solution is bubbled with nitrogen for 15 minutes. The solution is then cooled to 5° C. and $BF_3.Et_2O$ (1.1 eq.) is added. DDQ (1 eq.) is added in increments over 30 minutes. The reaction is monitored by TLC and more DDQ is added if reaction is not complete. At 15 minutes after DDQ addition, add another 0.1 g of DDQ followed by another 0.1 g addition at 18 minutes after first DDQ addition. At 30 minutes after initial DDQ addition, 0.3 mL of $BF_3.Et_2O$ is added followed by another 1 mL of $BF_3.Et_2O$ at 40 minutes. At 1 hour after initial DDQ addition is complete, no starting material was noticed by TLC and the reaction is quenched by the addition Zn powder and stirring of the reaction for 2 hours. The mixture is diluted with 200 mL of methanol and stirred for another hour. The mixture is diluted with water and extracted with chloroform. The organic fractions are dried over $MgSO_4$ and then concentrated. The product is purified by column chromatography.

Method 3:

Prophetic Example 17

Synthesis of 2,2'-(thieno[3,2-b]thiophene-2,5-diyl)bis(thiophene-3-carboxylic acid)

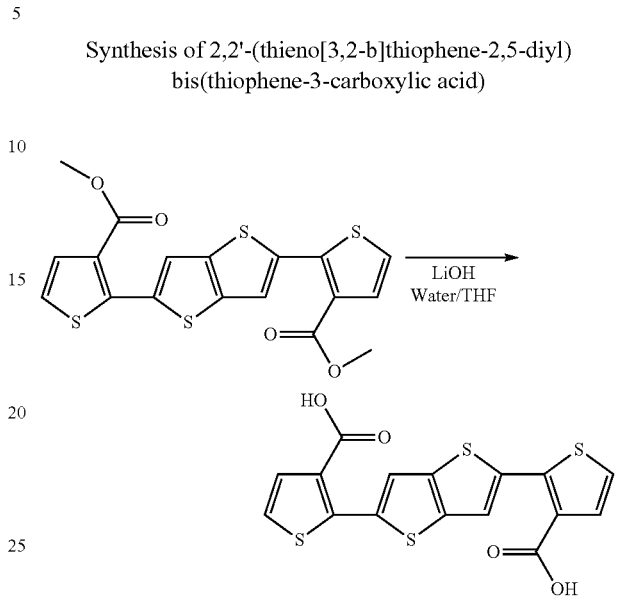

To a solution of the diester in THF, a 1M solution of lithium hydroxide is added. The mixture is refluxed overnight. After cooling to room temperature, THF was evaporated under vacuum. The aqueous phase was acidified with 5M HCl solution until PH=1. The formed precipitate is filtered and dried.

Prophetic Example 18

Synthesis of 2,2'-(thieno[3,2-b]thiophene-2,5-diyl)bis(thiophene-3-carbonyl chloride)

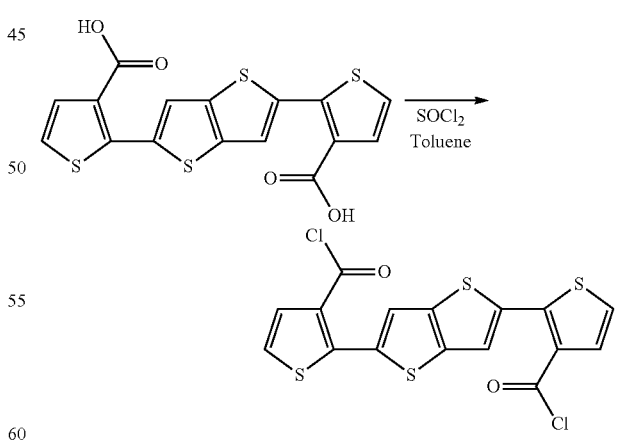

To a suspension of diacid in dry toluene are added two equivalents of thionyl chloride. The mixture was refluxed for one hour. Toluene and excess thionyl chloride are removed under vacuum. The resulting product is used without further purification.

Prophetic Example 19

Synthesis of BP3 diketone precursor

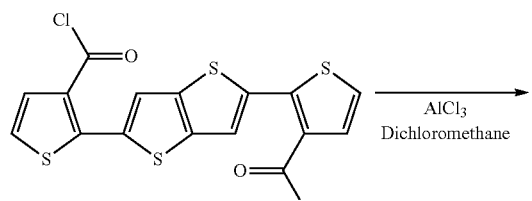

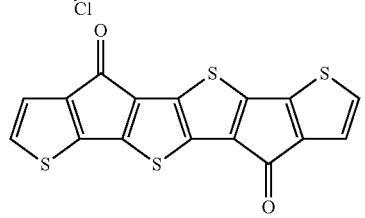

To a suspension of aluminum chloride in dry dichloromethane at 0° C. is added a solution of diacyl chloride in dry dichloromethane. The mixture is stirred for one hour at room temperature. The mixture is then poured onto ice. The aqueous phase is further extracted with dichloromethane. The combined organic phases are washed with water, then dried with magnesium sulfate and filtered through Buchner funnel. After evaporation the product is purified by column chromatography.

Prophetic Example

Synthesis of BP non alkylated precursor

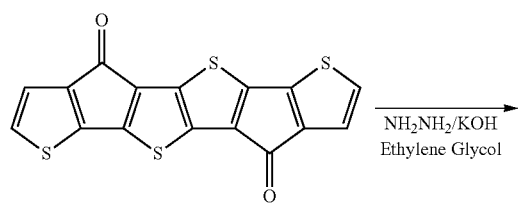

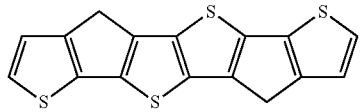

This conversion can be accomplished using the well-known Huang-Minlon modification of the Wolff-Kishner reaction, as described in Vogel's textbook of Organic Chemistry ($5^{th}$ Edition) page 820.

Prophetic Example

Synthesis of BP2

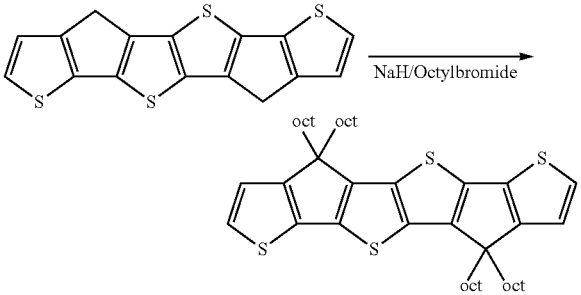

To a suspension of sodium hydride in THF is added a THF solution of starting material. Octyl bromide is then added and the mixture is refluxed until reaction completion, as determined by TLC. The reaction is then poured into cold water, extracted with MTBE. The combined organic phases are washed with water then dried with magnesium sulfate. After filtration through Buchner funnel the solvent is evaporated. The resulting product can be purified by column chromatography or recrystallization.

Also, forming part of the application written description:
APPENDIX A—LISTING OF POLYMERS
APPENDIX B—LISTING OF DONORS
APPENDIX C—LISTING OF ACCEPTORS

APPENDIX A.

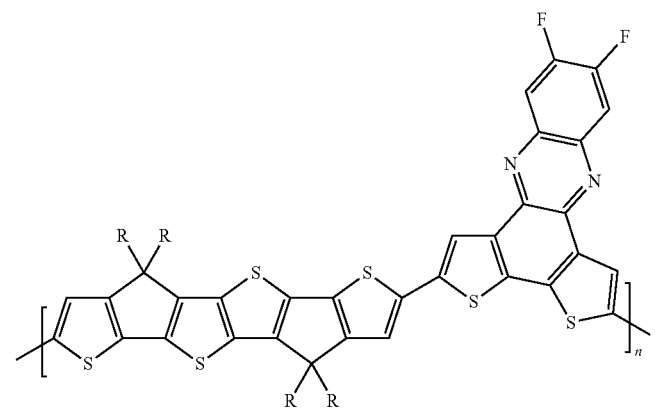

-continued
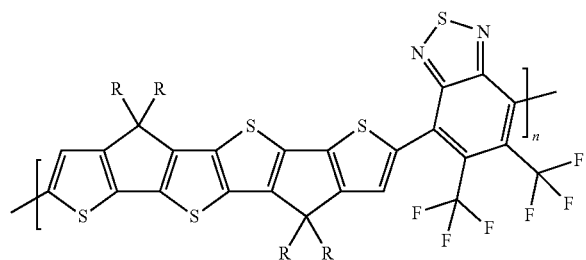
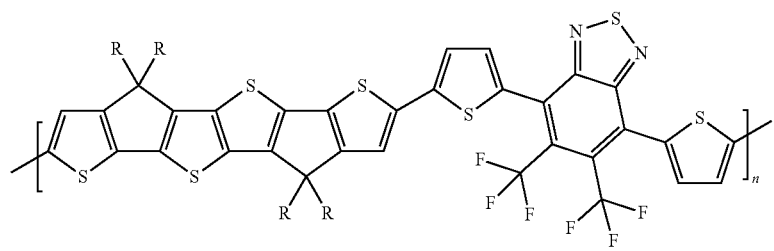
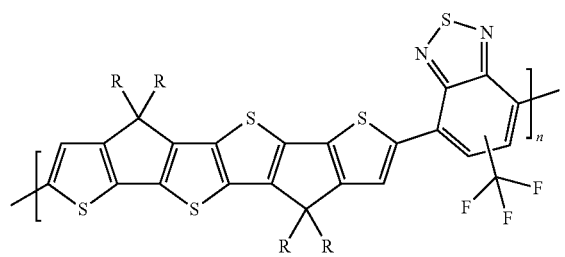
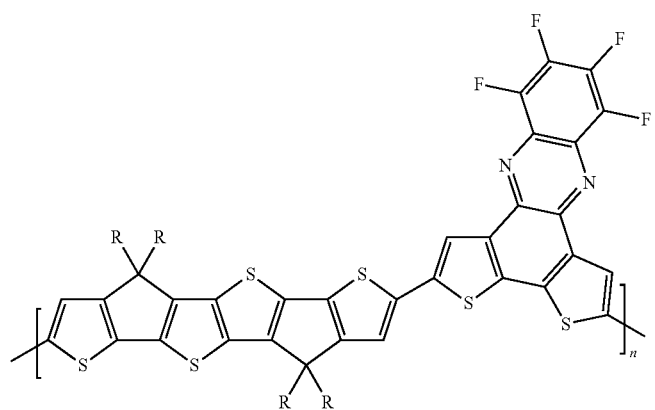
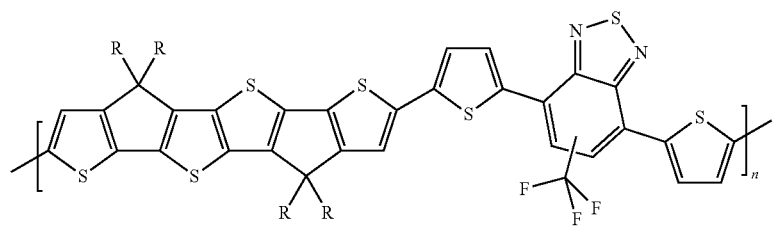

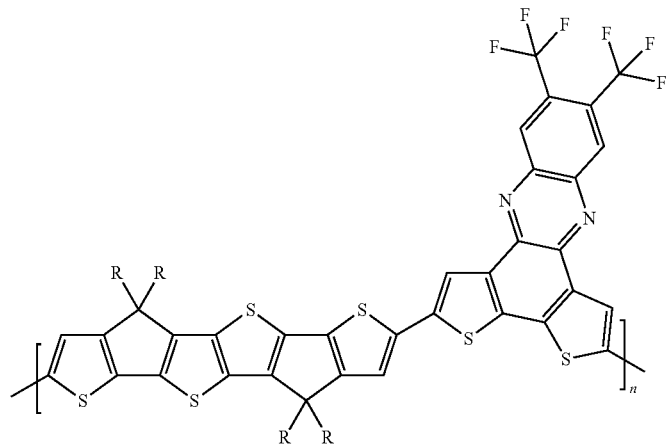
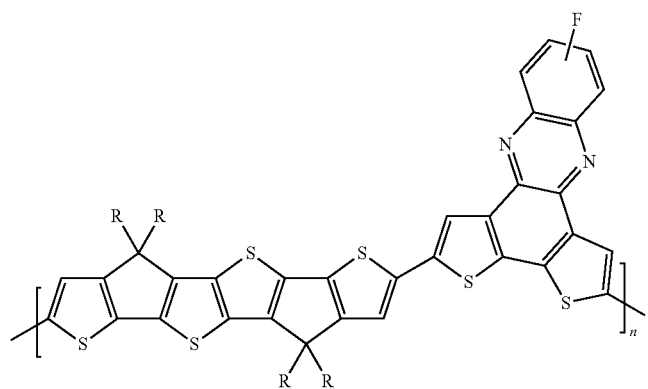
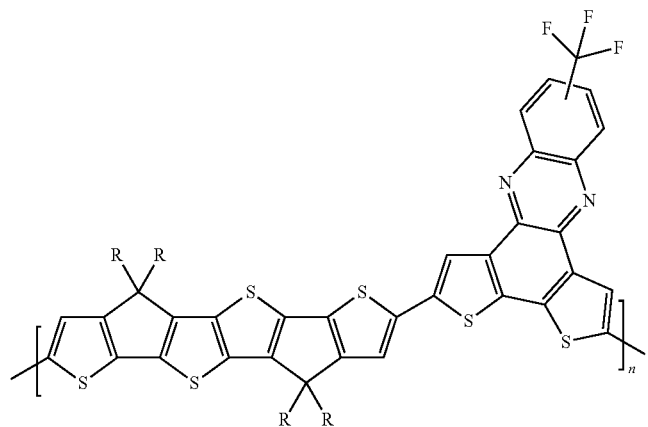
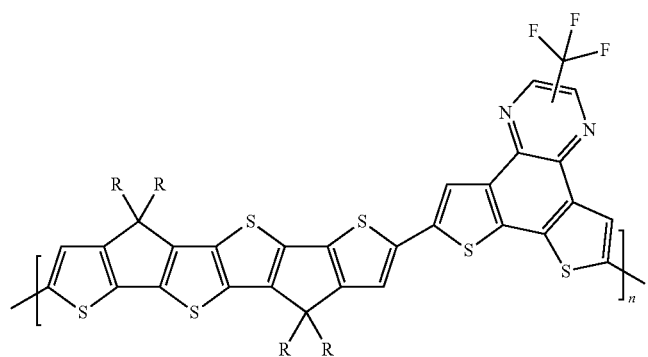

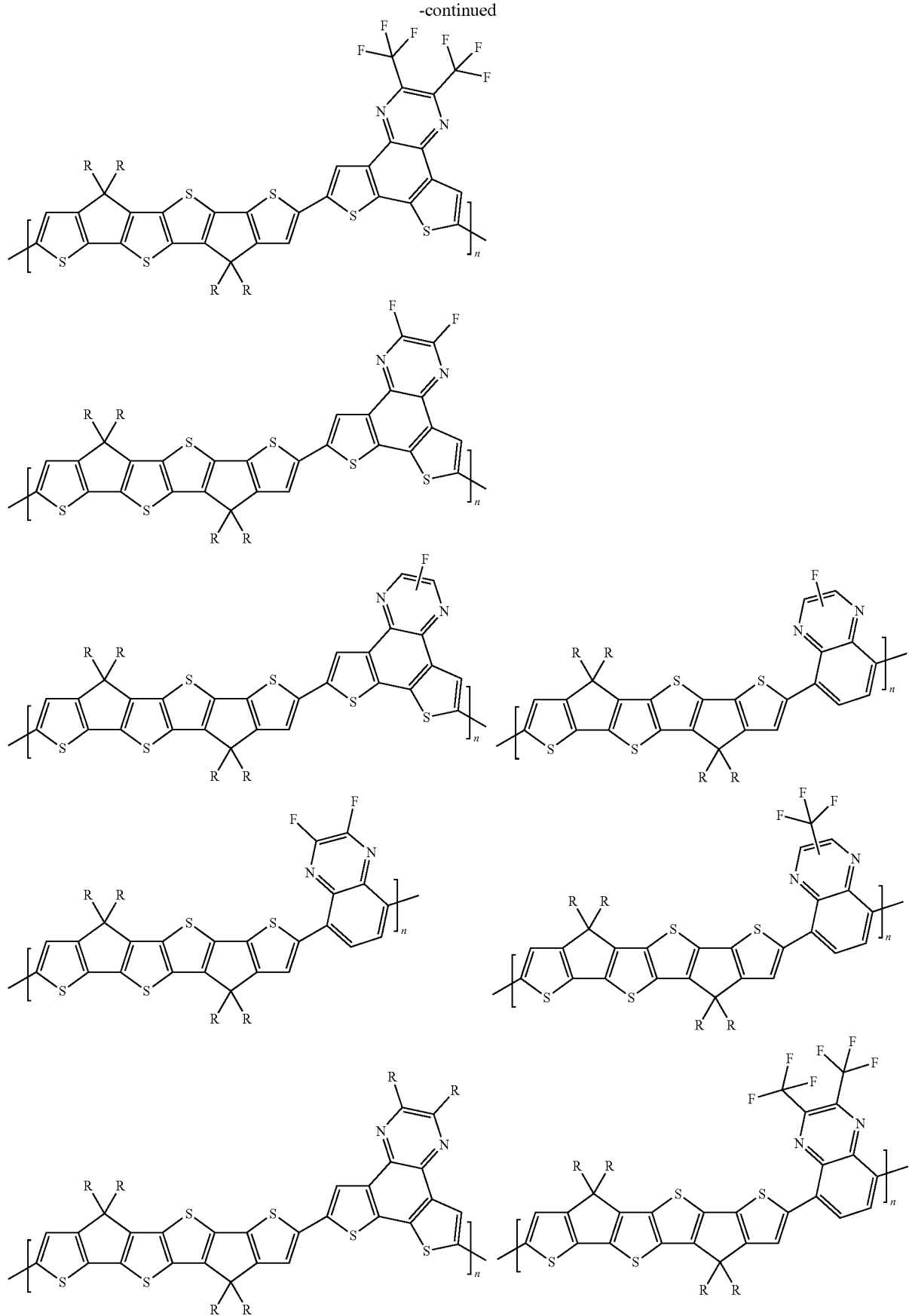

-continued
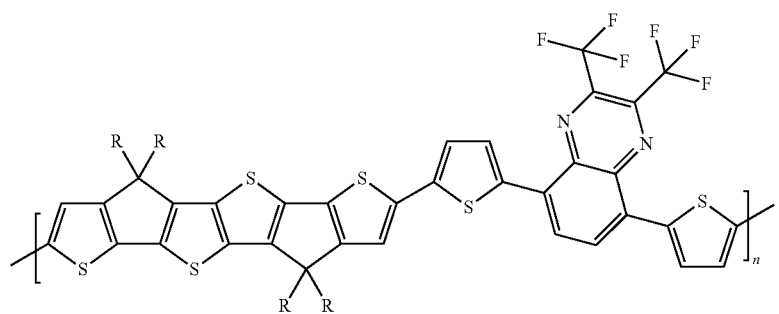
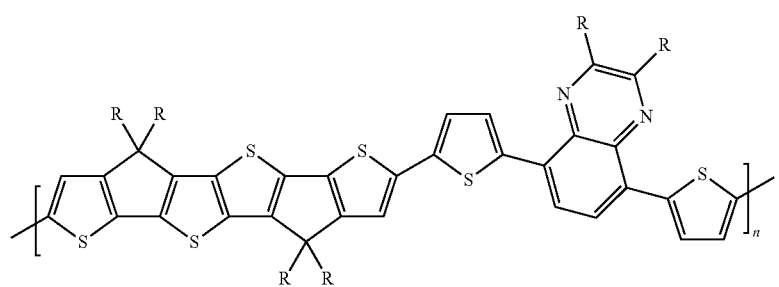
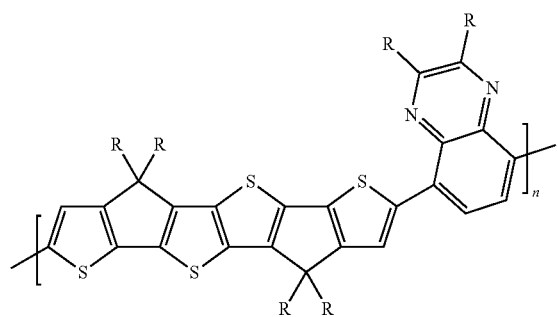
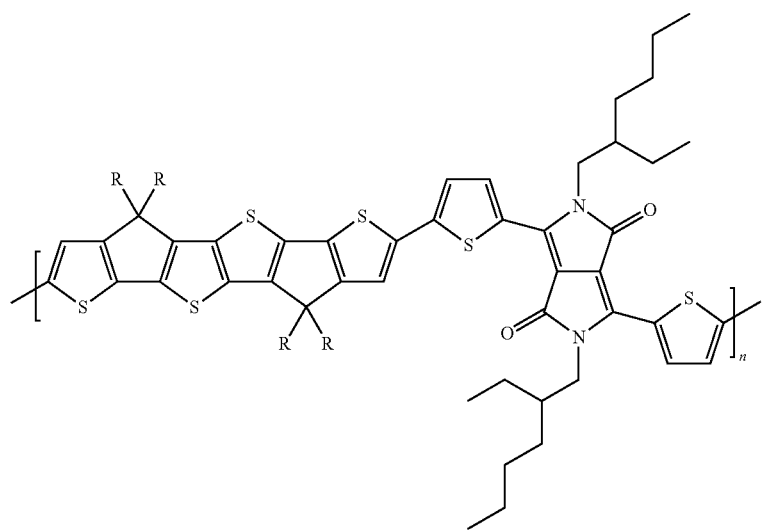

-continued
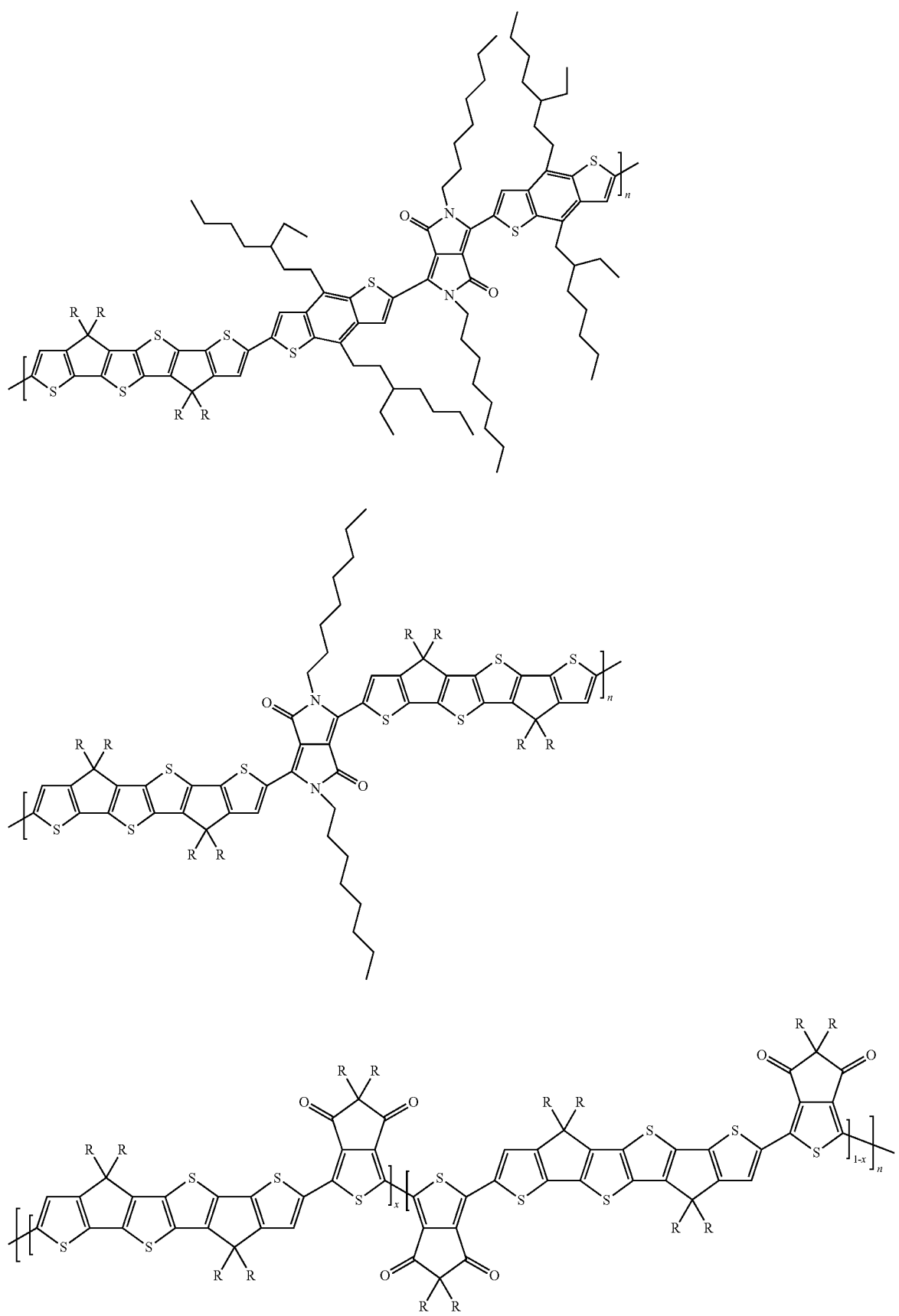

-continued
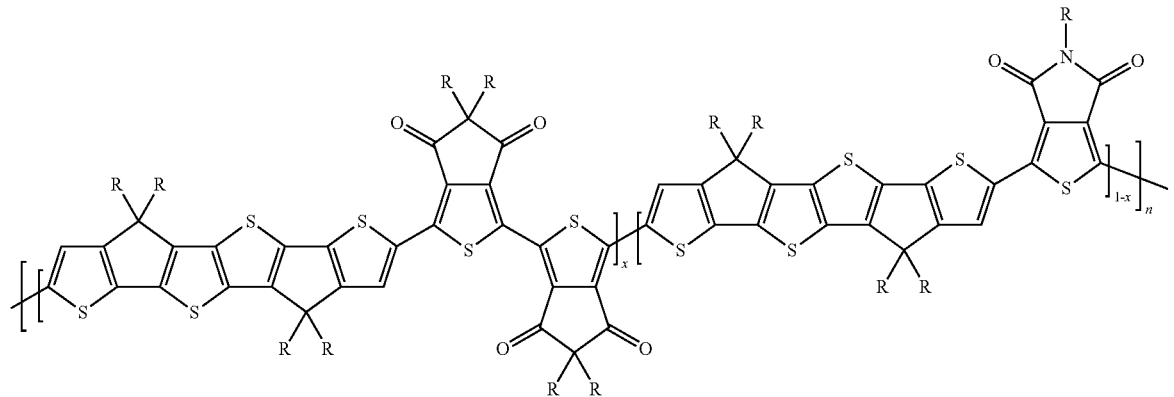
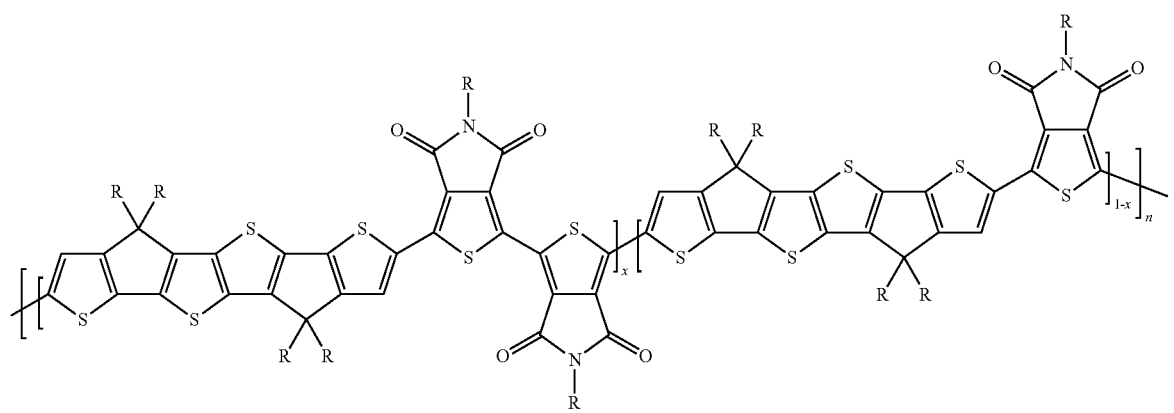
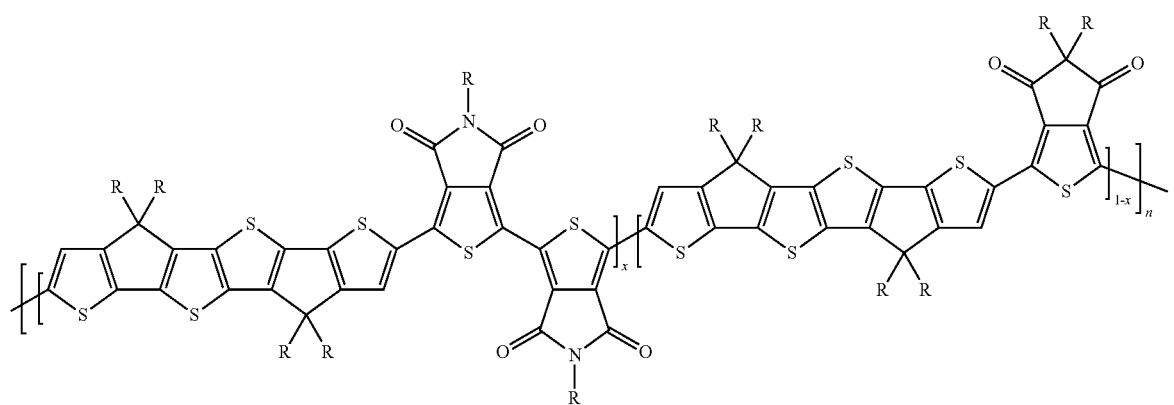
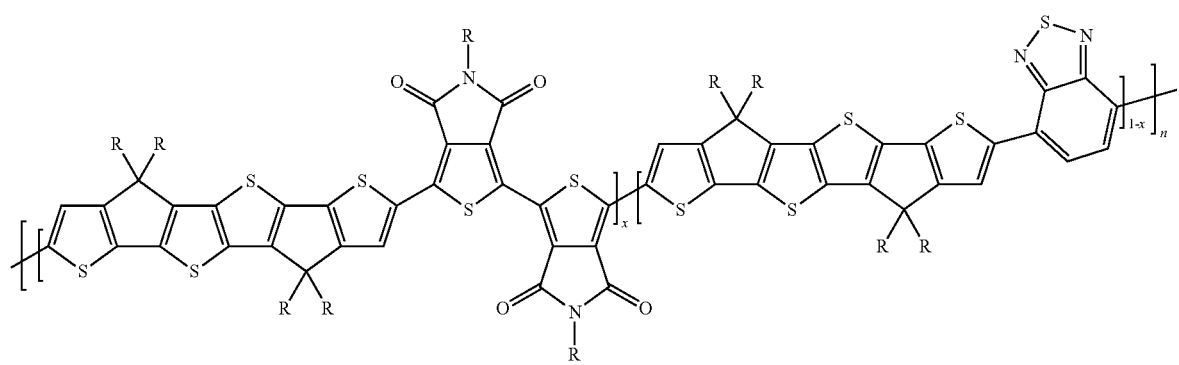

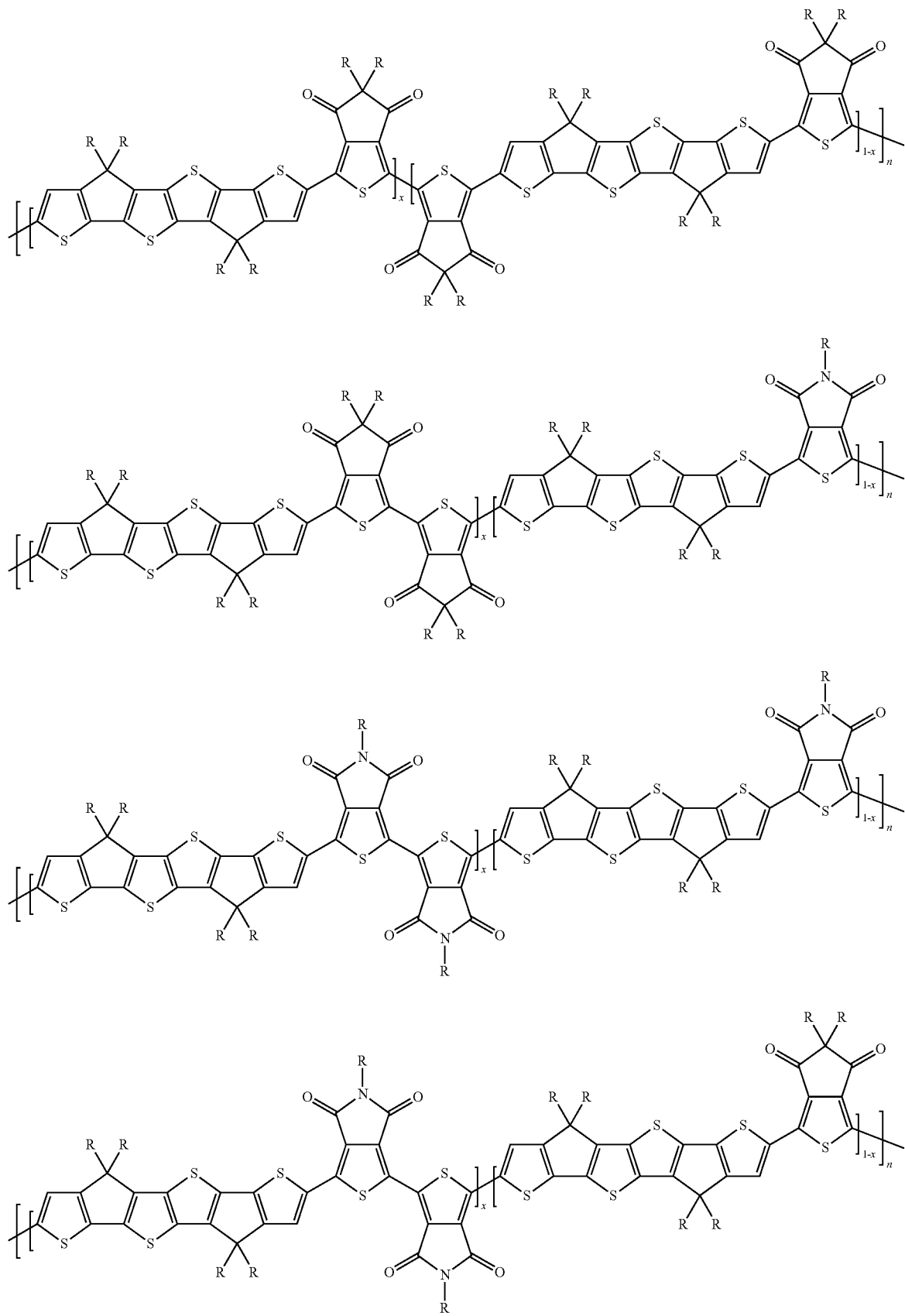

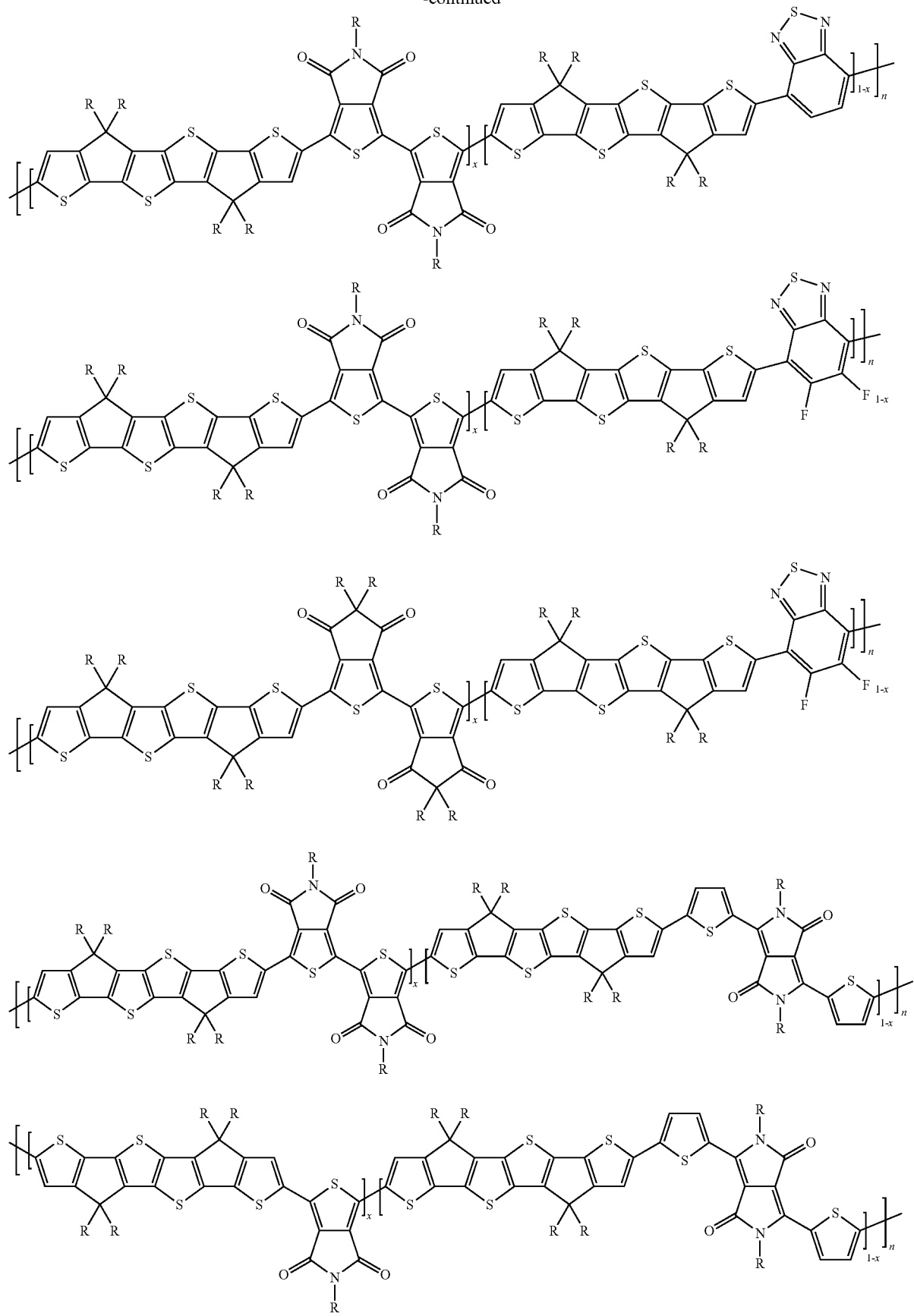

-continued
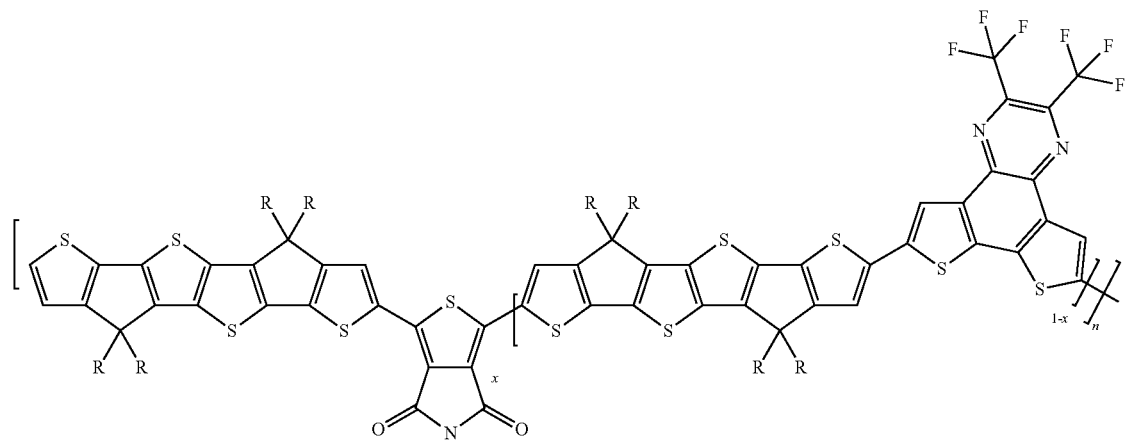
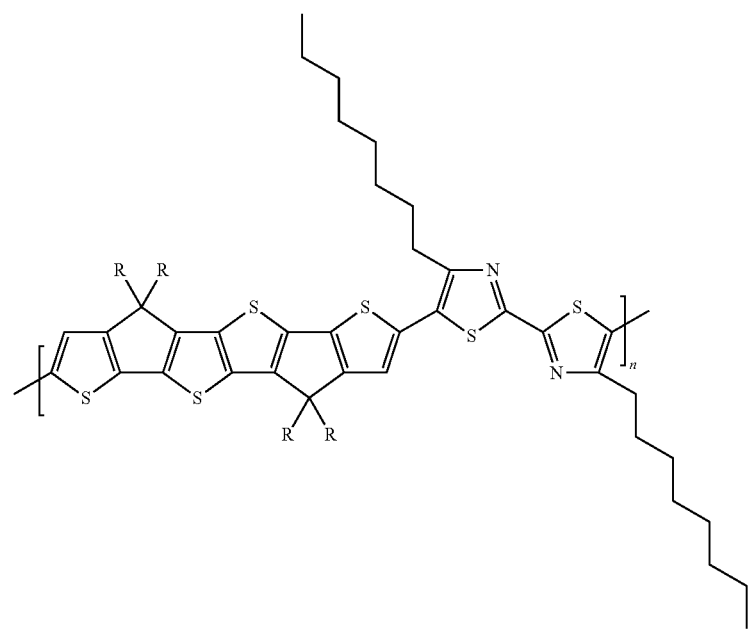
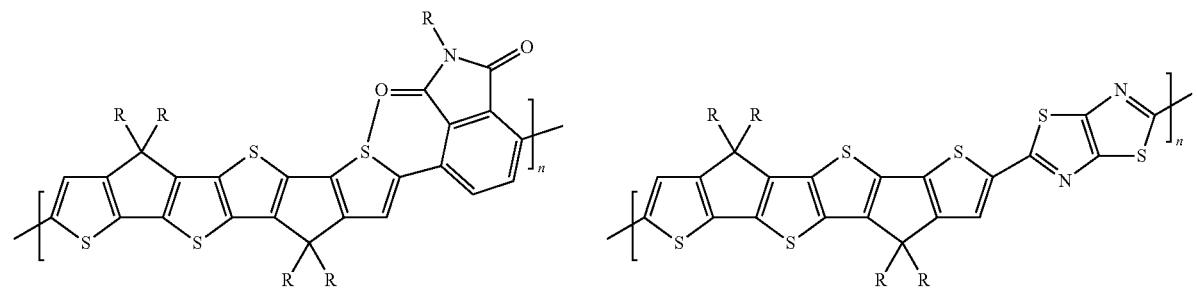

-continued
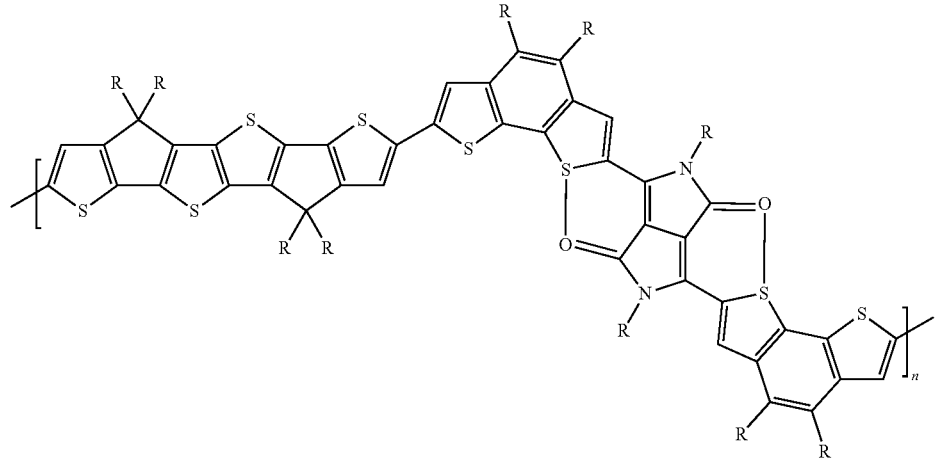
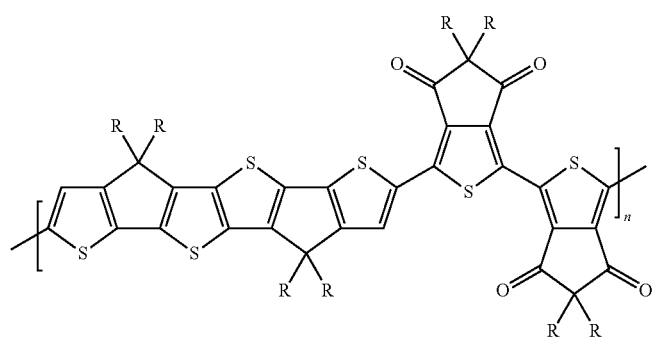
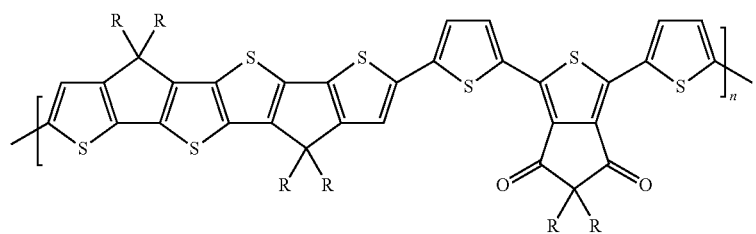
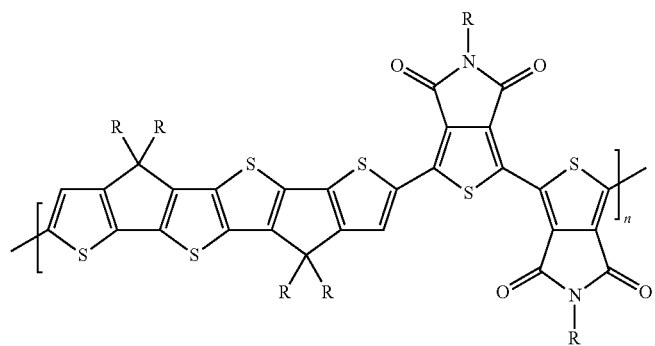
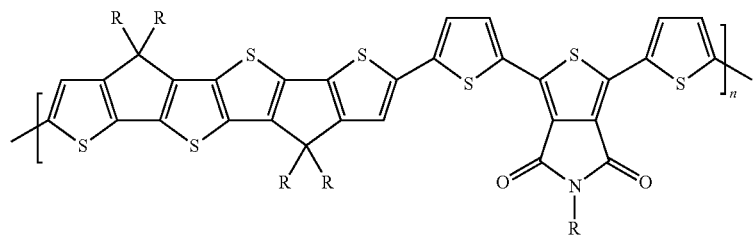

-continued
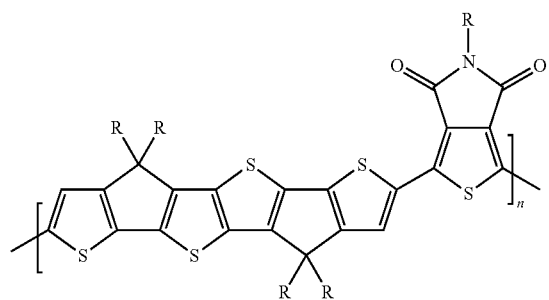
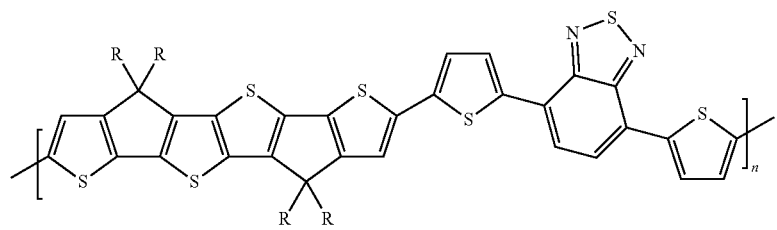
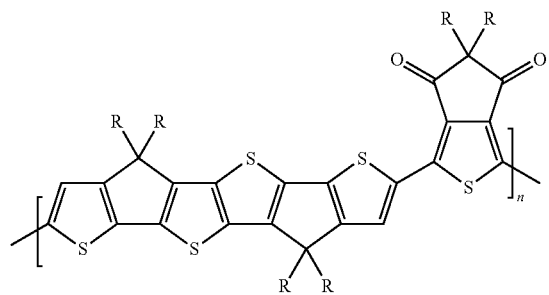
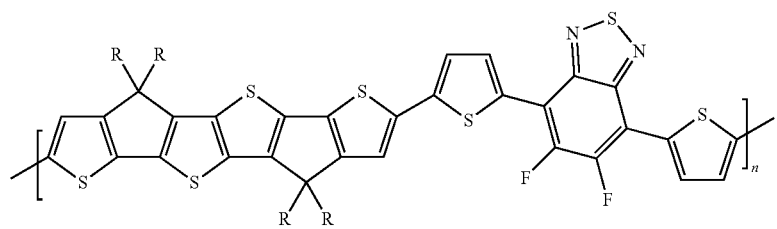
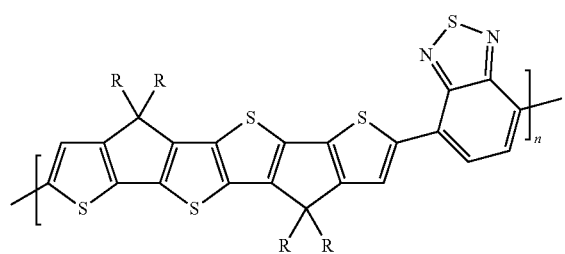
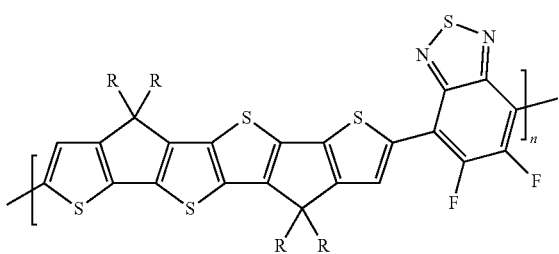
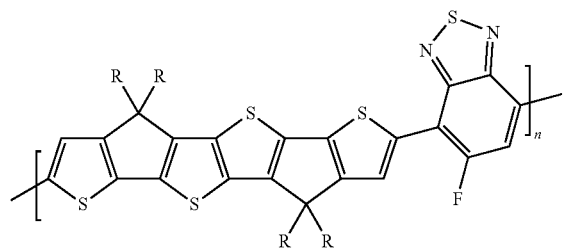
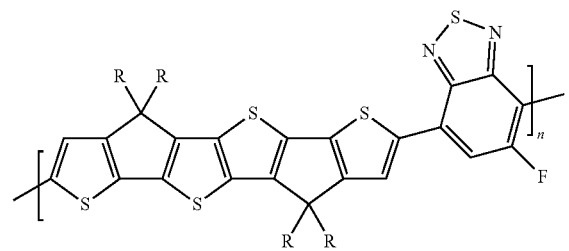

APPENDIX B
Donor
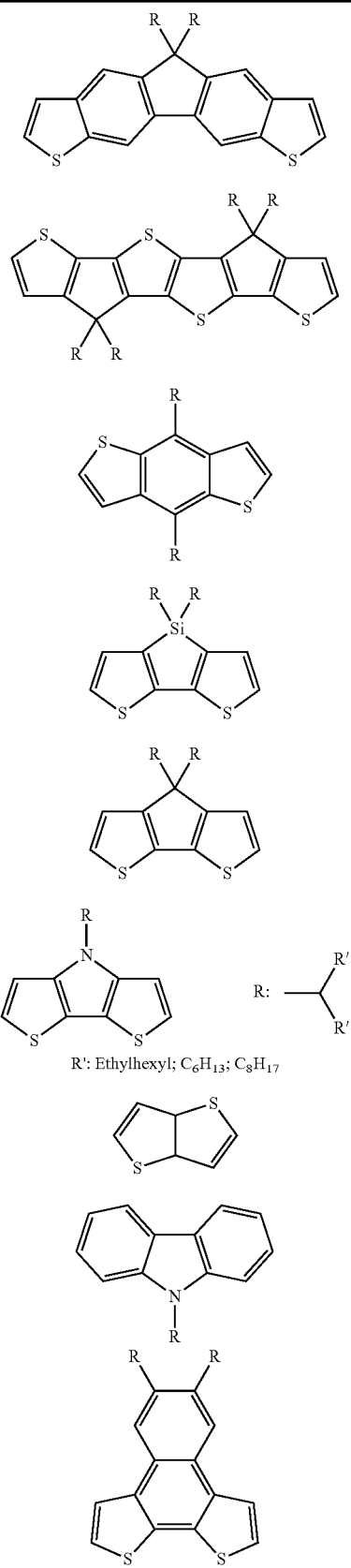
R': Ethylhexyl; C$_6$H$_{13}$; C$_8$H$_{17}$
APPENDIX B-continued
Donor
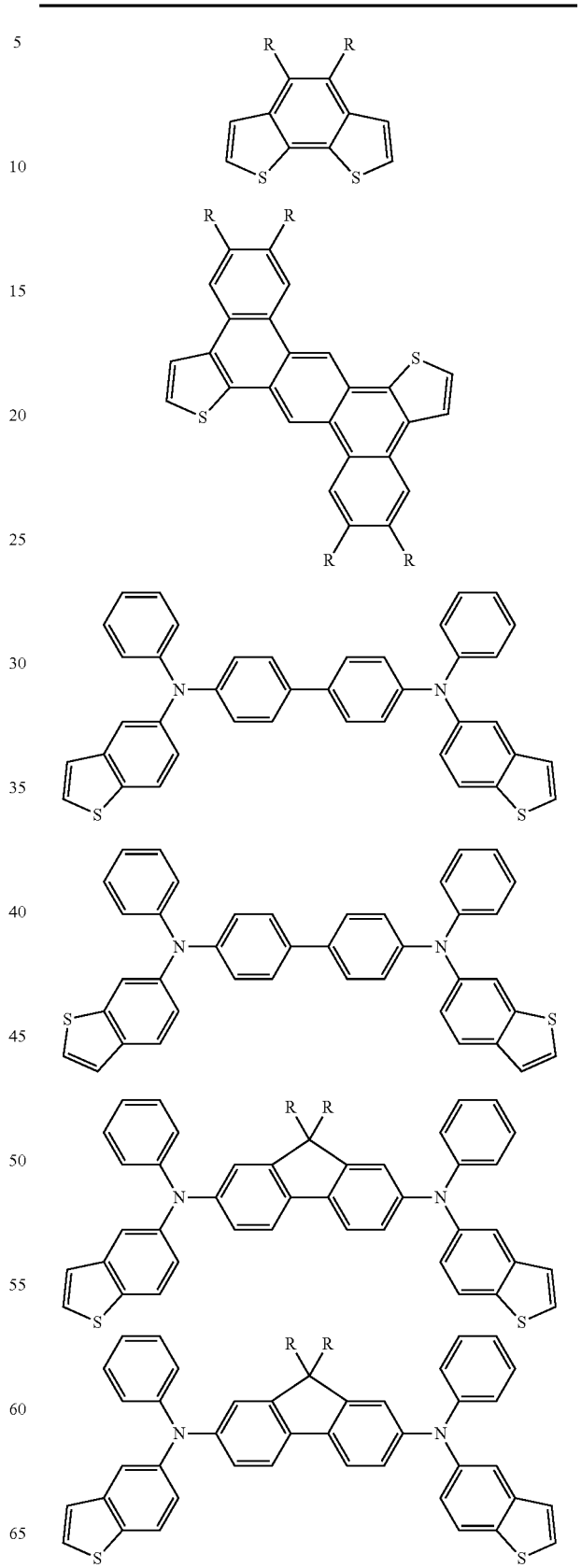

APPENDIX B-continued
Donor
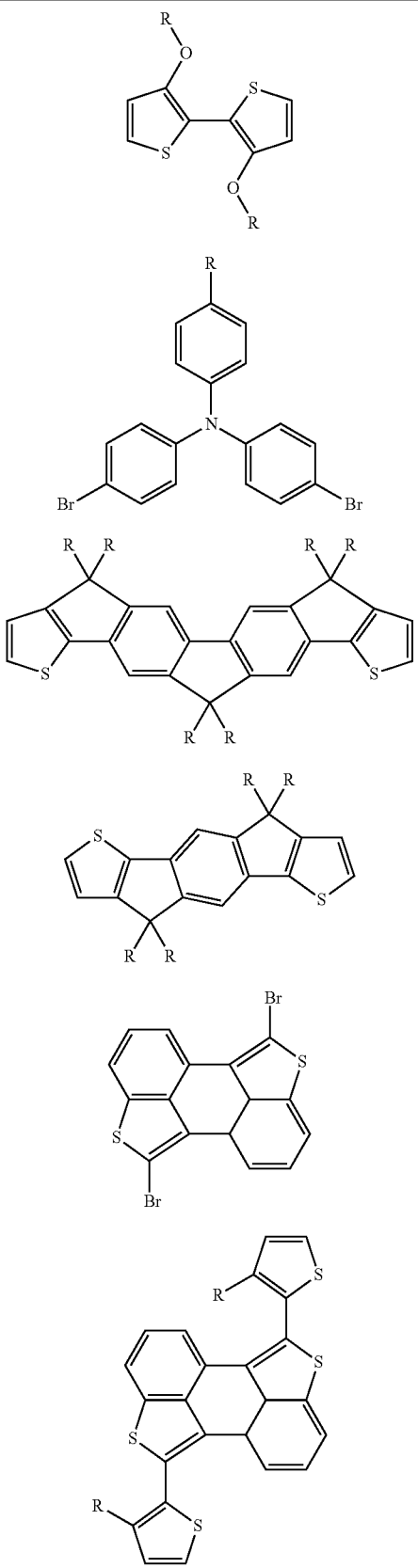
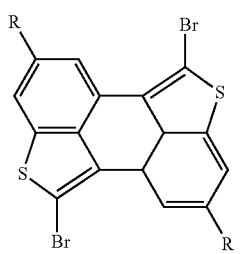
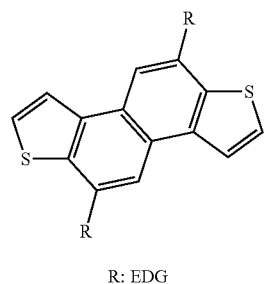
R: n-alkyl
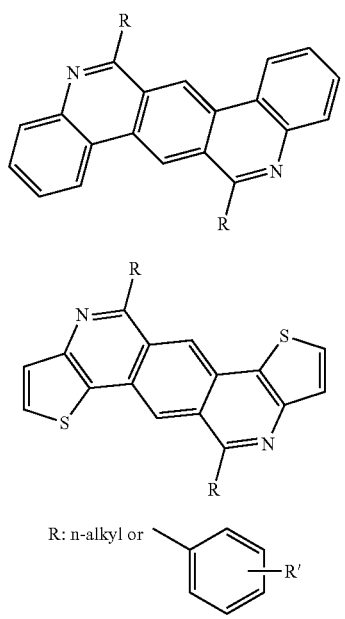
R: EDG
R: n-alkyl or

APPENDIX B-continued
Donor
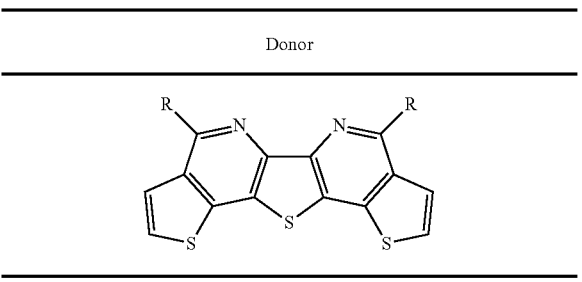
APPENDIX C
Acceptors
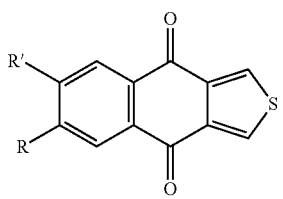
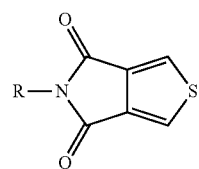
R: alkyl, branched alkyl, aromatic, EWG (e.g., fluorinated alkyl)
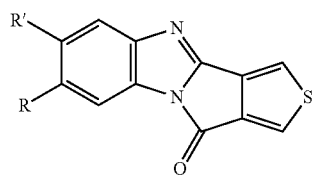
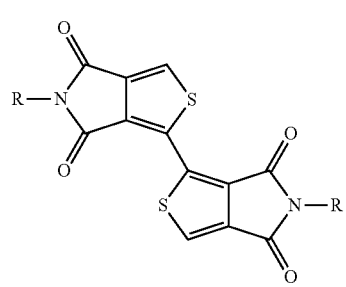
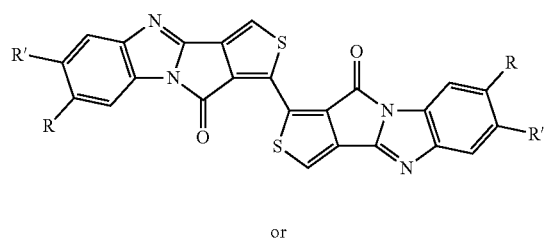
or
APPENDIX C-continued
Acceptors
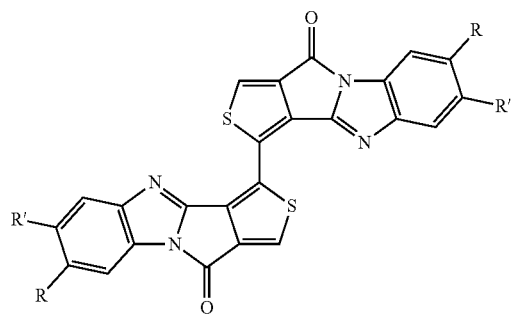
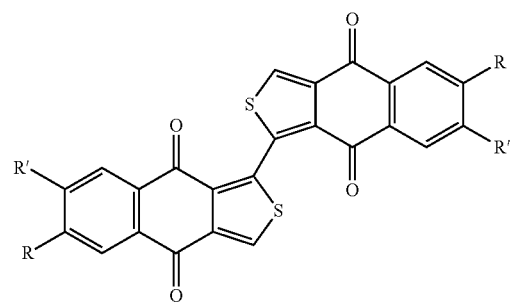
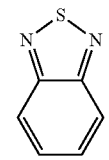
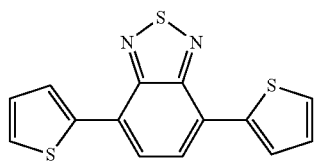 [SMILES: c1csc(-c2ccc(-c3cccs3)c3nsnc23)c1]
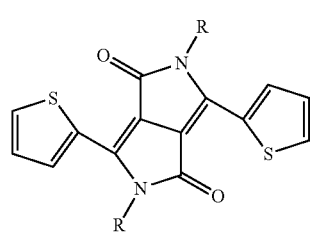
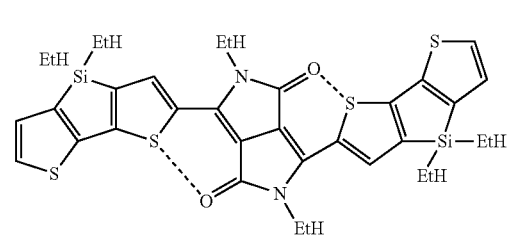

APPENDIX C-continued
Acceptors
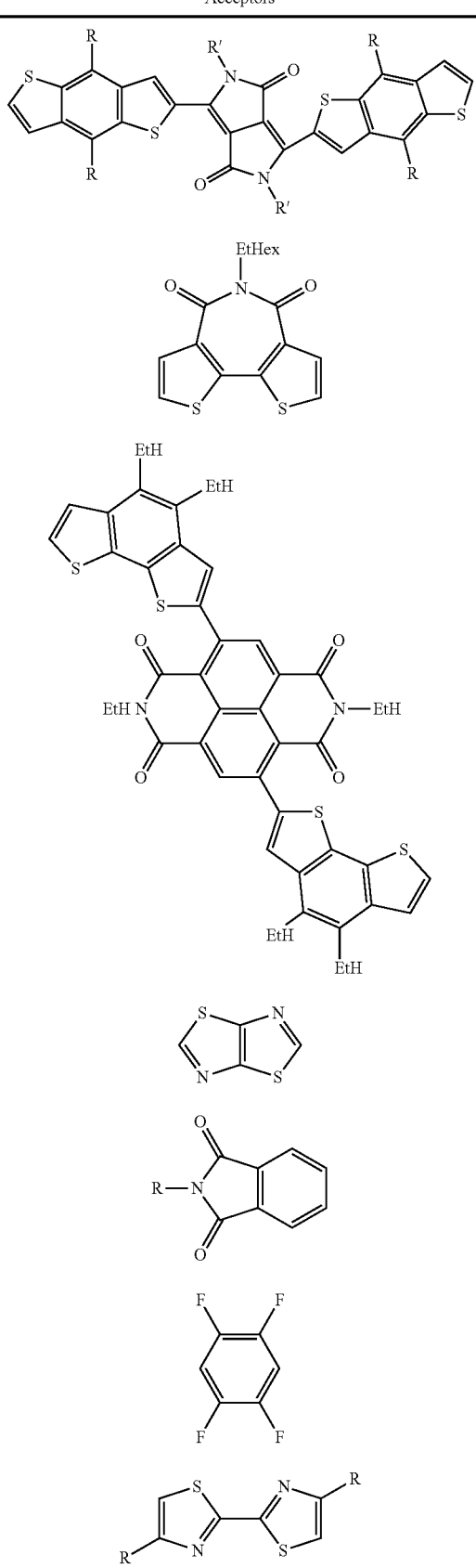
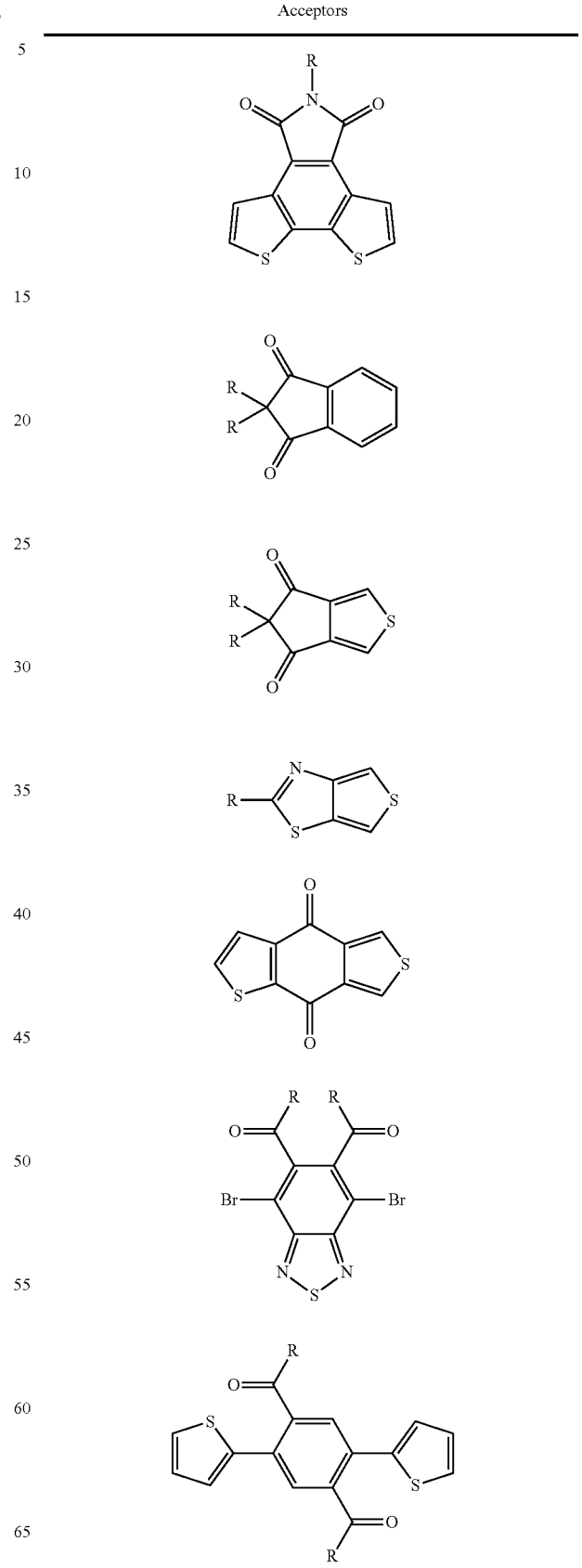

APPENDIX C-continued
Acceptors
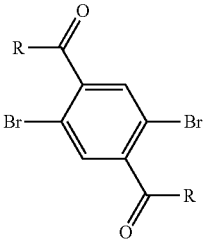
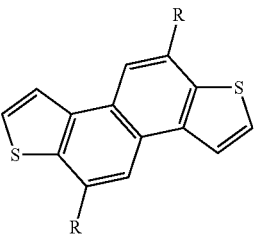
R: EWG
(e.g., diketobenzene analogues)
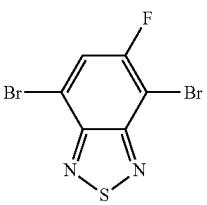 [SMILES: Fc1cc(Br)c2nsnc2c1Br]
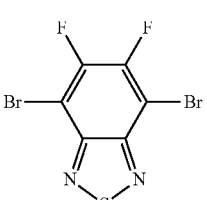
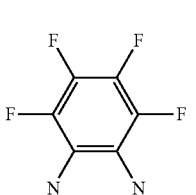
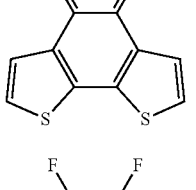
APPENDIX C-continued
Acceptors
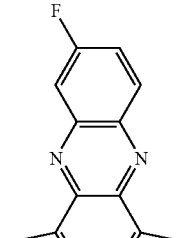
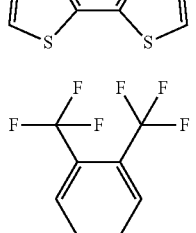
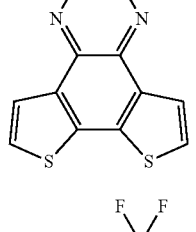
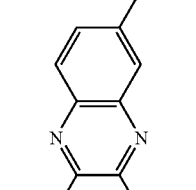
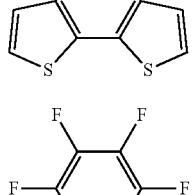

APPENDIX C-continued

Acceptors

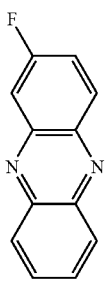 [SMILES: Fc1ccc2nc3ccccc3nc2c1]

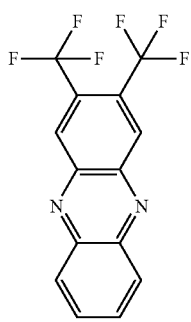 [SMILES: FC(F)(F)c1cc2nc3ccccc3nc2cc1C(F)(F)F]

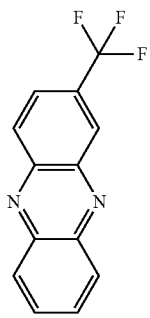 [SMILES: FC(F)(F)c1ccc2nc3ccccc3nc2c1]

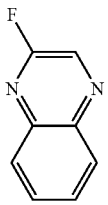 [SMILES: Fc1cnc2ccccc2n1]

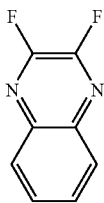 [SMILES: Fc1nc2ccccc2nc1F]

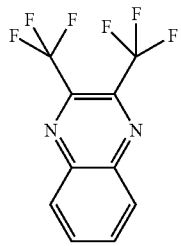 [SMILES: FC(F)(F)c1nc2ccccc2nc1C(F)(F)F]

APPENDIX C-continued

Acceptors

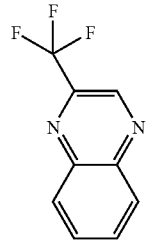 [SMILES: FC(F)(F)c1cnc2ccccc2n1]

What is claimed is:

1. An oligomer or polymer comprising:

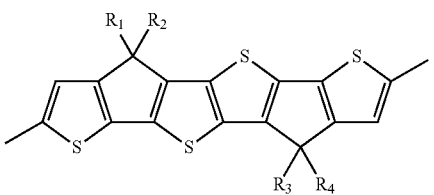

(I)

wherein $R_1$, $R_2$, $R_3$, and $R_4$ are independently hydrogen or solubilizing groups.

2. The oligomer or polymer of claim 1, wherein $R_1$, $R_2$, $R_3$, and $R_4$ are the same group.

3. The oligomer or polymer of claim 1, wherein $R_1$, $R_2$, $R_3$, and $R_4$ are the same group and comprise an aromatic group.

4. The oligomer or polymer of claim 1, wherein $R_1$, $R_2$, $R_3$, and $R_4$ are the same group and comprise an arylalkyl group.

5. The oligomer or polymer of claim 1, wherein it is as polymer having a molecular weight of at least 10,000 number average molecular weight.

6. The oligomer or polymer of claim 1, wherein the oligomer or polymer is a donor-acceptor oligomer or polymer.

7. The oligomer or polymer of claim 1, wherein the oligomer or polymer is a donor-acceptor polymer, and has at least two types of donors, or at least two types of acceptors.

8. The oligomer or polymer of claim 1, wherein the oligomer or polymer is soluble in chloroform, chlorobenzene, dichlorobenzene, or trichlorobenzene.

9. The oligomer or polymer of claim 1, wherein the oligomer or polymer has a molecular weight of at least 10,000 number average molecular weight and is soluble in chloroform, chlorobenzene, dichlorobenzene, or trichlorobenzene.

10. A coated substrate comprising at least one substrate and at least one coating, wherein the coating comprises at least one polymer according to claim 1.

11. A monomer comprising a moiety represented by:

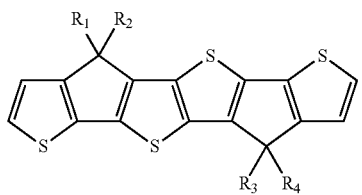

(II)

wherein $R_1$, $R_2$, $R_3$, and $R_4$ are independently hydrogen or solubilizing groups.

12. The monomer of claim 11, wherein $R_1$, $R_2$, $R_3$, and $R_4$ are the same group.

13. The monomer of claim 11, wherein $R_1$, $R_2$, $R_3$, and $R_4$ are the same group and comprise an aromatic group.

14. The monomer of claim 11, wherein $R_1$, $R_2$, $R_3$, and $R_4$ are the same group and comprise an arylalkyl group.

15. The monomer of claim 11, wherein the monomer is functionalized with electrophilic groups for polymerization.

16. The monomer of claim 11, wherein the monomer is functionalized with nucleophilic groups for polymerization.

17. The monomer of claim 11, wherein the monomer is functionalized for Ullman, Yamamoto, or Suzuki polymerization.

18. The monomer of claim 11, wherein the terminal thiophene rings are functionalized for polymerization.

19. An ink composition comprising at least one oligomer or polymer according to claim 1 and at least one solvent for the oligomer or polymer.

20. The ink composition of claim 19, wherein the $R_1$, $R_2$, $R_3$, and $R_4$ are the same group.

21. The ink composition of claim 19, wherein $R_1$, $R_2$, $R_3$, and $R_4$ are the same group and comprise an aromatic group.

22. The ink composition of claim 19, wherein $R_1$, $R_2$, $R_3$, and $R_4$ are the same group and comprise an arylalkyl group.

23. The ink composition of claim 19, wherein $R_1$, $R_2$, $R_3$, and $R_4$ are the same group and are a $C_1$-$C_{25}$ group.

24. The ink composition of claim 19, wherein the solvent comprises at least two solvents, and the ink composition further comprises at least one additive.

25. The ink composition of claim 19, wherein the solvent comprises a mixture comprising at least orthodichlorobenzene and trichlorobenzene.

26. A OPV device comprising at least one OPV active layer comprising at least one polymer comprising:

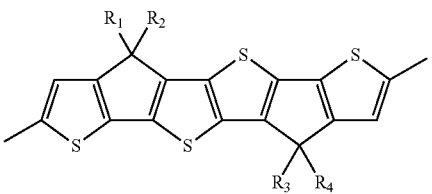

wherein $R_1$, $R_2$, $R_3$, and $R_4$ are independently hydrogen or solubilizing groups.

27. The device of claim 26, wherein the $R_1$, $R_2$, $R_3$, and $R_4$ are the same group.

28. The device of claim 26, wherein $R_1$, $R_2$, $R_3$, and $R_4$ are the same group and comprise an aromatic group.

29. The device of claim 26, wherein $R_1$, $R_2$, $R_3$, and $R_4$ are the same group and comprise an arylalkyl group.

30. The device of claim 26, wherein the polymer is a donor-acceptor polymer.

* * * * *